(12) United States Patent
Haj-Yehia

(10) Patent No.: US 7,378,438 B2
(45) Date of Patent: May 27, 2008

(54) BETA-AGONIST COMPOUNDS COMPRISING NITRIC OXIDE DONOR GROUPS AND REACTIVE OXYGEN SPECIES SCAVENGER GROUPS AND THEIR USE IN THE TREATMENT OF RESPIRATORY DISORDERS

(75) Inventor: Abdullah Ibrahim Haj-Yehia, Neve Shalom (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 24 days.

(21) Appl. No.: 10/512,024

(22) PCT Filed: Apr. 15, 2003

(86) PCT No.: PCT/IL03/00312

§ 371 (c)(1),
(2), (4) Date: May 9, 2005

(87) PCT Pub. No.: WO03/088961

PCT Pub. Date: Oct. 30, 2003

(65) Prior Publication Data

US 2005/0228184 A1  Oct. 13, 2005

Related U.S. Application Data

(60) Provisional application No. 60/374,173, filed on Apr. 19, 2002.

(51) Int. Cl.
*A61K 31/4035* (2006.01)
*C07D 209/44* (2006.01)

(52) U.S. Cl. .................. 514/416; 514/414; 548/467; 548/470

(58) Field of Classification Search .............. 514/414, 514/416; 548/467, 470
See application file for complete search history.

(56) References Cited

U.S. PATENT DOCUMENTS

| 4,166,452 | A | 9/1979 | Generales, Jr. |
|---|---|---|---|
| 4,256,108 | A | 3/1981 | Theeuwes |
| 4,265,874 | A | 5/1981 | Bonsen et al. |
| 4,992,474 | A | 2/1991 | Skidmore et al. |
| 5,277,195 | A | 1/1994 | Williams |
| 5,320,094 | A | 6/1994 | Laube et al. |
| 5,327,883 | A | 7/1994 | Williams et al. |
| 5,364,833 | A | 11/1994 | Kast et al. |
| 5,364,838 | A | 11/1994 | Rubsamen |
| 5,404,871 | A | 4/1995 | Goodman et al. |
| 5,419,315 | A | 5/1995 | Rubsamen |
| 5,492,112 | A | 2/1996 | Mecikalski et al. |
| 5,506,203 | A | 4/1996 | Bäckström et al. |
| 5,518,998 | A | 5/1996 | Bäckström et al. |
| 5,558,085 | A | 9/1996 | Rubsamen et al. |
| 5,577,497 | A | 11/1996 | Mecikalski et al. |
| 5,622,166 | A | 4/1997 | Eisele et al. |
| 5,645,051 | A | 7/1997 | Schultz et al. |
| 5,654,007 | A | 8/1997 | Johnson et al. |
| 5,655,523 | A | 8/1997 | Hodson et al. |
| 5,658,878 | A | 8/1997 | Bäckström et al. |
| 5,661,130 | A | 8/1997 | Meezan et al. |
| 5,672,581 | A | 9/1997 | Rubsamen et al. |
| 5,700,904 | A | 12/1997 | Baker et al. |
| 5,743,250 | A | 4/1998 | Gonda et al. |
| 5,780,014 | A | 7/1998 | Eljamal et al. |
| 5,821,259 | A | 10/1998 | Theoharides |
| 5,824,669 | A | 10/1998 | Garvey et al. |
| 6,060,069 | A | 5/2000 | Hill et al. |
| 6,083,993 | A | 7/2000 | Barberich et al. |
| 6,124,319 | A | 9/2000 | MacCoss et al. |
| RE37,116 | E | 3/2001 | Garvey et al. |
| 6,232,331 | B1 | 5/2001 | Sankaranarayanan |
| 6,238,647 | B1 | 5/2001 | Akehurst et al. |
| 6,241,969 | B1 | 6/2001 | Saidi et al. |
| 6,248,895 | B1 | 6/2001 | Sankaranarayanan |
| 6,254,882 | B1 | 7/2001 | Jerussi |
| 6,297,762 | B1 | 10/2001 | Labitt |
| 6,299,863 | B1 | 10/2001 | Aberg et al. |
| 6,335,316 | B1 | 1/2002 | Hughes et al. |

(Continued)

FOREIGN PATENT DOCUMENTS

AU          733202 B2      10/1997

(Continued)

OTHER PUBLICATIONS

Johansson et al., "b2-Adrenoceptor selectivity in four series of b-adrenoceptor agonists," European Journal of Pharmacology, vol. 130(1-2), pp. 97-103 (1986).*

(Continued)

*Primary Examiner*—Rebecca L Anderson
*Assistant Examiner*—Jason M Nolan
(74) *Attorney, Agent, or Firm*—Roach Brown McCarthy & Gruber, P.C.; Kevin D. McCarthy

(57) ABSTRACT

The present invention relates to multifunctional β-agonist compounds comprising a reactive oxygen species scavenger group and a nitric oxide donor, and their use for the treatment of respiratory diseases involving airway obstruction, such as asthma and chronic bronchitis. The invention further relates to methods and devices for administering the compounds.

14 Claims, 1 Drawing Sheet

U.S. PATENT DOCUMENTS

| | | | |
|---|---|---|---|
| 6,369,071 | B1 | 4/2002 | Haj-Yehia |
| 6,448,267 | B1 | 9/2002 | Anggard et al. |
| 6,455,542 | B1 | 9/2002 | Anggard et al. |
| 6,492,405 | B2 | 12/2002 | Haj-Yehia |
| 6,642,260 | B2 | 11/2003 | Haj-Yehia |
| 6,759,430 | B2 | 7/2004 | Anggard et al. |
| 2001/0041190 | A1 | 11/2001 | Ward et al. |
| 2002/0006901 | A1 | 1/2002 | Iacono |
| 2002/0034477 | A1 | 3/2002 | Edwards et al. |
| 2004/0147598 | A1 | 7/2004 | Haj-Yehia |

FOREIGN PATENT DOCUMENTS

| | | |
|---|---|---|
| GB | 2 349 385 A | 11/2000 |
| WO | WO-95/24183 A1 | 9/1995 |
| WO | WO-95/30641 A1 | 11/1995 |
| WO | WO-96/32149 A1 | 10/1996 |
| WO | WO-96/32946 A1 | 10/1996 |
| WO | WO-96/39409 A1 | 12/1996 |
| WO | WO-97/25984 A1 | 7/1997 |
| WO | WO-97/31654 A1 | 9/1997 |
| WO | WO-97/34871 A1 | 9/1997 |
| WO | WO-98/33480 A1 | 8/1998 |
| WO | WO-98/42661 A1 | 10/1998 |
| WO | WO-98/55453 A1 | 12/1998 |
| WO | WO-99/37616 A1 | 7/1999 |
| WO | WO-99/40787 A1 | 8/1999 |
| WO | WO-99/61018 A1 | 12/1999 |
| WO | WO-99/61430 A1 | 12/1999 |
| WO | WO-99/62509 A1 | 12/1999 |
| WO | WO-99/66918 A1 | 12/1999 |
| WO | WO-00/31060 A1 | 6/2000 |
| WO | WO-00/35434 A2 | 6/2000 |
| WO | WO-00/35434 A3 | 6/2000 |
| WO | WO-00/53191 A2 | 9/2000 |
| WO | WO-00/53191 A3 | 9/2000 |
| WO | WO-00/67754 A1 | 11/2000 |
| WO | WO-01/32202 A1 | 5/2001 |
| WO | WO-03/088961 A1 | 10/2003 |

OTHER PUBLICATIONS

Johansson et al., "β2-Adrenoceptor selectivity in four series of β-adrenoceptor agonists," European Journal of Pharmacology, vol. 130(1-2), pp. 97-103 (1986).*

Anonymous (Nov. 3, 1990). "Editorials: β2 Agonists in Asthma: Relief, Prevention, Morbidity," Lancet 336(8723):1411-1412.

Boushey, H.A. (1998). "Bronchodilators & Other Agents Used in Asthma," Chapter 20 In Basic & Clinical Pharmacology Seventh Edition, Katzung, B.G. ed. Appleton and Lange: Stamford, CT pp. 325-342.

Burrows, B. et al. (Feb. 20, 1992). "The β-Agonist Dilemma," The New England Journal of Medicine 326(8):560-561.

Costello, J.F. ed. (1997). Sympathomimetic Enantiomers in the Treatment of Asthma The Parthenon Publishing Group, Inc.: London. (Table of Contents Only.).

Cotran, R.S. et al. (1989). "The Respiratory System" Chapter 16 In Robbins Pathologic Basis of Disease Fourth Edition, W.B. Saunders Co.: Philadelphia, PA pp. 755-797.

Haahtela, T. et al. (Aug. 8, 1991). "Comparison of a B2-Agonist, Terbutaline, With an Inhaled Corticosteroid, Budesonide, in Newly Detected Asthma," The New England Journal of Medicine 325(6):388-392.

Haj-Yehia, A. et al. (Jul./Aug. 2000). "Development of 3-Nitratomethyl-PROXYL (NMP): A Novel, Bifunctional Superoxide Dismutase-Mimic-Nitric Oxide-Donor," Drug Development Research 50(3/4):528-536.

Hansel, T. et al. ed. (2001). New Drugs for Asthma, Allergy and COPD Karger: London, vol. 31, pp. v-vii (Table of Contents Only.).

Hett, R. et al. (1994). "Enantioselective Synthesis of Salmeterol via Asymmetric Borane Reduction," Tetrahedron Letters 35(50):9375-9378.

Hett, R. et al. (1997). "Enantio- and Diastereoselective Synthesis of all Four Stereoisomers of Formoterol," Tetrahedron Letters 38(7):1125-1128.

Hoffman, B.B. (1998). "Adrenoceptor-Activating & Other Sympathomimetic Drugs," Chapter 9 In Basic & Clinical Pharmacology Seventh Edition, Katzung, B.G. ed. Appleton and Lange: Stamford, CT pp. 118-151.

Jansen, A. et al. (1992). "The Relaxant Properties in Guinea Pig Airways of S-Nitrosothiols," J. Pharmacol. Exptl. Therapeutics 261(1):154-160.

Kaminsky, D.A. et al. (Oct. 1999). "Nitrotyrosine Formation in the Airways and Lung Parenchyma of Patients with Asthma," J. Allergy Clin. Immunol. 104(4/1):747-754.

Murray, J.F. et al. eds. (Oct.-Nov. 1979). American Review of Respiratory Disease 120(4/5) (Table of Contents Only.).

Rees, J. (May 18, 1991). "B2 Agonists and Asthma," British Medical Journal 302(6786):1166-1167.

Robak, J. et al. (1993). "Nitric Oxide Donors as Generators and Scavengers of Superoxide Anions," Pol. J. Pharmacol. 45(1):51-58.

Robak, J. et al. (Dec. 20, 1993). "Nitric Oxide Donors as Generators and Scavengers of Superoxide Anions," Chemical Abstracts 25:71 Abstract No. 119:262465b.

Shiraishi, M. et al. (Oct. 14, 1996). "Drugs for Improvement of Lipid Metabolism," Chemical Abstracts 125(16):649 Abstract No. 125:204523g.

Spitzer, W.O et al. (Feb. 20, 1992). "The Use of β-Agonists and the Risk of Death and Near Death From Asthma," The New England Journal of Medicine 326(8):501-506.

Svedmyr, N. et al. (1990). "The Current Place of β2-Agonists in the Management of Asthma," Lung 168(Supp):105-110.

Tamaoki, J. et al. (Jun. 1995). "Role of NO Generation in β-Adrenoceptor-Mediated Stimulation of Rabbit Airway Ciliary Motility," Am. J. Physiol. 268(6):C1342-C1346.

Thompson, R.F. et al. (Jul.-Aug. 1985). "Hypersensitivity Vasculitis Associated With Streptokinase," Clin. Pharm. 4(4):383-386.

Wagner, A.F. et al. (Oct. 5, 1956). "Properties and Derivatives of α-Lipoic Acid," Journal of the American Chemical Society 78:5079-5081.

Wolf, E.W. et al. (1998). "Reversal of Cerebral Vasospasm Using an Intrathecally Administered Nitric Oxide Donor," J. Neurosurg. 89(2):279-288.

* cited by examiner

BETA-AGONIST COMPOUNDS COMPRISING NITRIC OXIDE DONOR GROUPS AND REACTIVE OXYGEN SPECIES SCAVENGER GROUPS AND THEIR USE IN THE TREATMENT OF RESPIRATORY DISORDERS

This application is a National Phase under 35 U.S.C. §371 of International Application No. PCT/IL03/00312 filed Apr. 15, 2003 and published in English on Oct. 30, 2003, which claims the benefit of U.S. Provisional Application Ser. No. 60/374,173, filed Apr. 19, 2002, the disclosure of which are incorporated herein by reference in its entirety.

FIELD OF THE INVENTION

The present invention relates to multifunctional β-agonist compounds that are capable of acting both as nitric oxide donors and as scavengers of reactive oxygen species and which are useful in the treatment of respiratory disorders. The invention further relates to methods of using such compounds in the treatment of respiratory disorders such as asthma.

BACKGROUND OF THE INVENTION

NO (nitric oxide) is formed from the amino acid L-arginine by several forms of NO synthases, and plays a role in a number of physiological functions, including the relaxation of airway smooth muscle. NO formed in endothelial cells in response to chemical agonists and to physical stimuli plays a key role in regulation of vascular tone, platelet aggregation and adhesion, as well as modulating smooth muscle proliferation (Haj-Yehia et al. (2000) *Drug. Development Res.* 50:528-536). NO overproduction has also been associated with numerous disease states (WO 99/66918). NO levels have been shown to be increased in the asthmatic airways (Kaminsky et al. (1999) *J. Allergy Clin. Immunol* 104(4)I:747-754). The role of NO in the respiratory system has been studied (Tamaoki et al. (1995) *Am. J. Physiol.* 268(6)I:C1342-C1346). NO has also been used in the treatment of asthmatics, though such treatments demonstrated a great deal of inter- and intra-individual variability (WO 01/32202).

Publications disclosing nitric oxide donor compounds or compounds which promote the synthesis of nitric oxide include WO 98/42661, WO 99/37616, WO 00/31060, WO 97/34871, WO 00/35434, WO 99/62509, WO 97/25984, WO 00/67754, WO 9961018, WO 99/61430, WO 97/31654, WO 96/32946, WO 00/53191, U.S. Pat. Nos. 6,248,895 and 6,232,331 and Wolf et al. (1998) *J. Neurosurg.* 89:279-288. Publications disclosing nitric oxide scavenger compounds include WO 98/55453.

The endothelium, in addition to producing NO, also produces superoxide (SO) anion and other reactive oxygen species (ROS) under physiological conditions. Despite SO being a reducing agent that is itself incapable of initiating oxidative reactions, SO is considered the most important source of oxidative stress. Compounds for the removal of SO are described in the art, including WO 96/39409 and U.K. Pat. App. No. 2349385A.

Many disease states, including diabetes mellitus and various cardiovascular diseases, are associated with oxidative stress and endothelial dysfunction. Nitroglycerin (GTN) has been used for the treatment of various types of myocardial ischemia Because of its pathogenic nature (chronicity with acute exacerbation), prophylactic and acute treatments are necessary to prevent complications with potentially fatal outcomes (>25% death for acute MI). However, the phenomenon of tolerance to the anti-anginal effects of GTN and to all other existing organic nitrates is of a special clinical significance. In particular, early development of tolerance to the drug is by far the most serious drawback of nitrate therapy.

A number of respiratory disorders have been recognized. Many of which have overlapping and interacting etiologies. The majority of these disorders are characterized by acute pulmonary vasoconstriction or bronchoconstriction. Inflammation and edema are also often associated with respiratory disorders such as asthma, respiratory distress syndrome (child or adult), bronchitis, pneumonia and others.

Various compounds and treatments for respiratory disorders are disclosed in the art, for example, in U.S. Pat. Nos. 6,299,863, 6,124,319, 6,297,762, 6,254,882, 6,083,993, 5,824,669, 5,821,259, RE 37,116E, WO 97/34871, WO 01/32202, WO 99/40787, WO 95/30641 and Australian Patent No. 733202.

At the therapeutic level, $\beta_2$-agonists are the first drugs that are used in the acute treatment of asthma (Roberts et al, *Lung* (1990) 168:Suppl. 105-110, and Rees, *BMJ* (1991) 302: 1166-7). It is more controversial whether they should be used for chronic maintenance therapy (Haahtela et al., *NEJM* (1991) 325:388-92 and Burrows and Lebowitz, *NEJM* (1992) 326:560-1). Several effective $\beta_2$-agonists are currently available. However, patients may respond better to one drug over another so it is reasonable to switch drugs if a patient is not responding (Thompson et al., *Clin Pharm.* 1985; 4:383-8). The inhaled route of administration is the preferred route and a metered dose inhaler is the preferred way of administering the drug by inhalation. Methods of making aerosol formulations of β-agonists are known in the art, as described for example in U.S. Pat. No. 6,238,647.

Most $\beta_2$-agonists cause somewhat similar adverse effects. These adverse effects include but are not limited to cardiovascular effects such as palpitations, increased heart rate, and tachycardia; central nervous system symptoms such as nervousness, dizziness, headache and drowsiness; respiratory side effects such as dyspnea, wheezing, drying or irritation of the oropharynx, coughing, chest pain and chest discomfort; hand tremors, muscle tremors, and immediate hypersensitivity reactions such as urticaria, angioedema, rash and even bronchospasms. In addition, some $\beta_2$-agonists can cause angina, vertigo, central stimulation and insomnia, airway hyperreactivity (hypersensitivity), nausea, diarrhea, dry mouth and vomiting (see also Boushey, "Basic & Clinical Pharmacology" 7th Ed., pp. 118-151 and 325-342, Katzung, Ed. 1998, Appleton & Lange, Stamford, Conn.). N-agonists may sometimes cause systemic adverse effects such as weakness, fatigue, flushed feeling, sweating, unusual taste, hoarseness, muscle cramps and backaches.

Furthermore, patients have a tendency to develop a tolerance to the bronchodilating effect of β-agonists. This is related to desensitization, which is one of the most clinically significant phenomena involving the β-adrenergic receptor. It has been observed that patients in prolonged β-agonist therapy have a tendency to increase the dosage their medication. This occurs because after prolonged administration, the β-receptor appears to become desensitized to the agonist, thus requiring larger doses of the compound to effect an equivalent physiological response. Often an increase in dosage leads to an increase in the kind, number or severity of adverse effects (see e.g. Paterson et al: *American Review* of *Respiratory Disease* (1979) 120:844-1187); *Lancet* (1990) 336:1411-1412; Spitzer et al. *New England J. Med.* (1992).

There is a need for improved drugs for the treatment of respiratory disorders such as asthma

SUMMARY OF THE INVENTION

The present invention relates to multifunctional β-agonist compounds that are capable of acting both as nitric oxide donors and as scavengers of reactive oxygen species and which are useful in the treatment of respiratory disorders. The invention further relates to methods of using such compounds in the treatment of respiratory disorders such as asthma.

In one embodiment a multifunctional β-agonist compound is provided comprising a β-agonist component, at least one antioxidant, such as a reactive oxygen species (ROS) scavenger component, and at least one nitric oxide donor component.

In one embodiment a multifunctional β-agonist compound is provided comprising a β-agonist for the treatment of respiratory disorders linked to at least one reactive oxygen species (ROS) scavenger and at least one nitric oxide donor.

In certain embodiments, the β-agonist provided is based on modified salbutamol, salmetrol, fometeral, or terbutalin.

In other embodiments of the compounds as described herein the compound comprises at least two nitric oxide donors.

In other embodiments of the compounds as described herein, the nitric oxide donor is independently selected from the group consisting of —ONO, —ONO$_2$, —SNO and —NONOate.

In still other embodiments, the antioxidant, such as an ROS scavenger, is a substituted nitroxide free radical; alkenyl group; aryl group; substituted aryl group, where the aryl group is substituted with, for example, —OH, —NH$_2$, —NHCHO or a NO donor group; or a group that is, or is capable of being converted in vivo into, a sulfhydryl in oxidized or reduced form.

Compounds in one embodiment are provided of Formula 1:

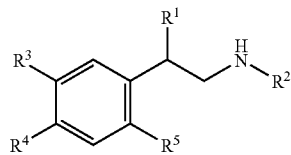

wherein R$^1$ is selected from the group consisting of —OH, —ONO, —ONO$_2$, —SNO, and —NONOate;

R$^2$ is optionally substituted alkyl; or a group comprising an ROS scavenger and optionally an NO-donor;

R$^3$ and R$^4$ are independently selected from the group consisting of —OH, —CH$_2$OH, —NH$_2$, and —NHCHO; or R$^3$ and R$^4$ together form a substituted 5 to 7-membered saturated heterocycle having 1 or 2 heteroatoms independently selected from nitrogen, and oxygen, and sulfur, e.g. a substituted pyrrolidine, substituted oxazolidine or substituted piperidine; or R$^3$ and R$^4$ together form amino or hydroxy protecting groups selected from N-formyl, acetal, and ketal; and R$^5$ is selected from the group consisting of —H, —OH, —CH$_2$OH, —NH$_2$, —NHCHO, straight or branched chain C$_1$-C$_3$ alkyl and straight or branched chain C$_1$-C$_3$ alkoxy;

whereas said RO scavenger moieties are optionally substituted with one or more C$_1$-C$_{15}$ alkyl groups, C$_1$-C$_{15}$ alkoxy groups, phenyl, —NH$_2$, —NHCHO, —OH, —CH$_2$OH, and groups capable of donating NO in a charged or neutral form; and whereas any of said alkyl groups is optionally substituted with one or more functional groups selected from hydroxyl, bromo, fluoro, chloro, iodo, mercapto or thio, cyano, alkylthio, aryl, carboxyl, carbalkoyl, alkenyl, nitro, amino, alkoxyl, amido;

wherein at least one of R$^1$, R$^2$, R$^3$ or R$^4$ comprises at least one ROS scavenger; and wherein at least one of R$^1$, R$^2$, R$^3$ or R$^4$ comprises at least one NO donor.

In certain embodiments of the compound described by the above formula, R$^1$ is —ONO$_2$ or —SNO.

In other embodiments of the compound as described by the above formula R$^2$ is substituted with —ONO$_2$ or —SNO.

In other embodiments of the compounds of Formula 1, R$^3$ and R$^4$ together form a substituted pyrrolidine, substituted oxazolidine or substituted piperidine N-oxide free radical.

Other embodiments include compounds having the formula

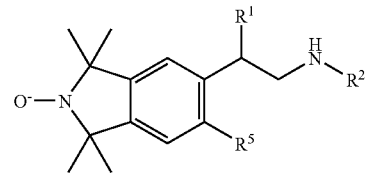

wherein R$^1$ is selected from the group consisting of —OH, —ONO, —ONO$_2$, —SNO, and —NONOate;

R$^2$ is optionally substituted alkyl; or a group comprising an antioxidant and optionally an NO-donor;

wherein R$^2$ is optionally substituted with —ONO, —ONO$_2$, or —SNO; and

R$^5$ is selected from the group consisting of —H, C$_1$-C$_3$ alkyl, C$_1$-C$_3$ alkoxy, —OH, —CH$_2$OH, —NH$_2$, and —NHCHO.

In particular embodiments of the compound as described by the above formula, R$^1$ is —ONO$_2$ or —SNO.

In other embodiments of the compound as described by the above formula, R$^2$ comprises an aryl group.

In still other embodiments of the compounds as described by the above formulas, R$^2$ is selected from the group consisting of t-butyl,

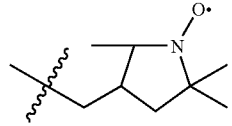

-continued

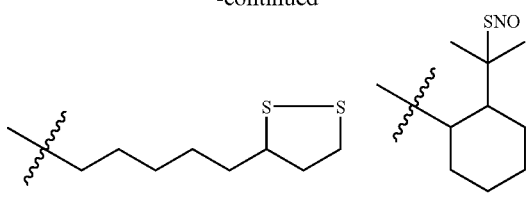

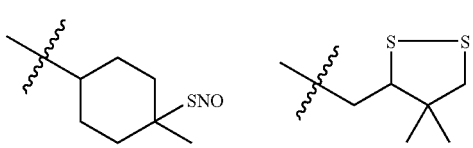

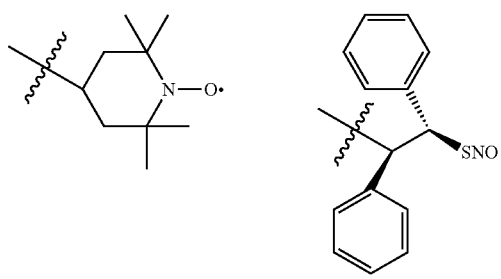

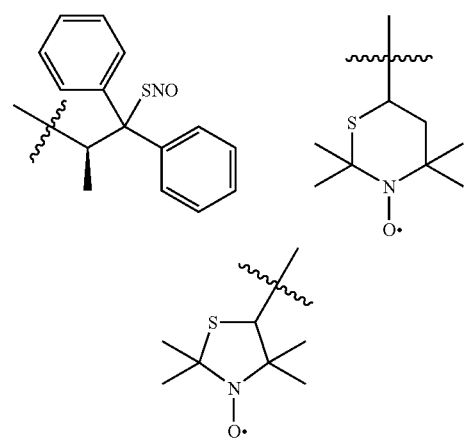

In one embodiment, the following compounds, and methods for their use in the treatment of respiratory disorders are provided:

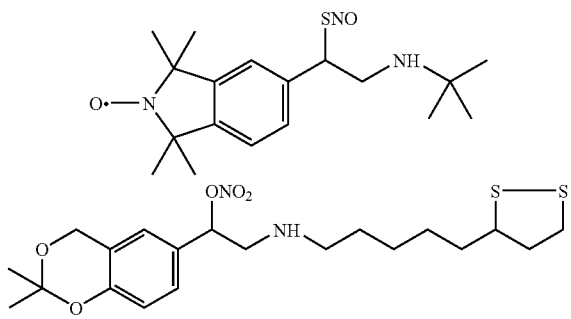

-continued

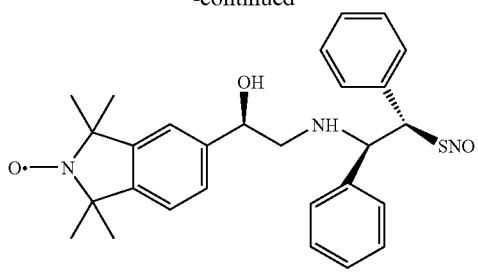

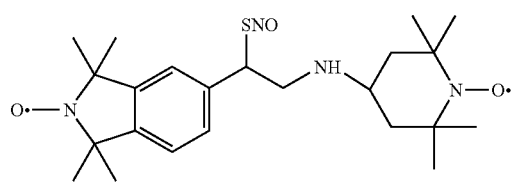

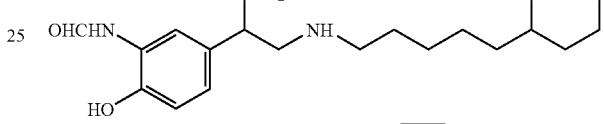

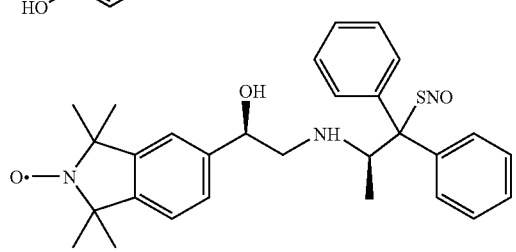

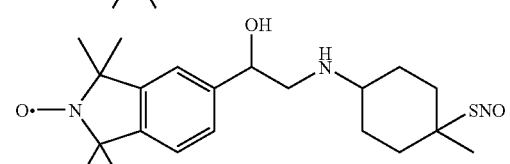

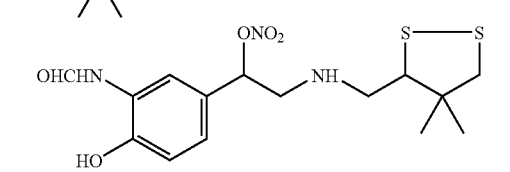

and salts thereof.

Included in the scope of the present invention are compositions comprising the compounds as described herein and a pharmaceutically acceptable excipient.

Also included herein are methods of treating a respiratory condition in an individual in need thereof comprising administering a therapeutically effective amount of a compound as described herein to said individual.

The present invention provides the compounds of the present invention for use in therapy.

The present invention further provides use of the compounds of the present invention in the manufacture of a medicament for the treatment of respiratory disorders.

In certain embodiments of the methods described herein, a compound or composition as described herein is administered is orally. The compound or composition may be administered by inhalation.

In some embodiments of the methods described herein, the respiratory condition is asthma, chronic obstructive pulmonary disease, bronchial hyperreactivity, adult respiratory distress syndrome, emphysema, bronchopulmonary dyspasia, or interstitial pulmonary fibrosis.

Certain embodiments include an inhalation device comprising a compound as described herein. In still other embodiments, a kit is provided for the treatment of respiratory disorders including a multifunctional β-agonist compound, an inhalation device, and optionally, appropriate packaging, labeling and/or instructions for use, wherein the inhalation device is optionally a metered dose inhaler.

DETAILED DESCRIPTION OF THE PREFERRED EMBODIMENTS

Figure 1:
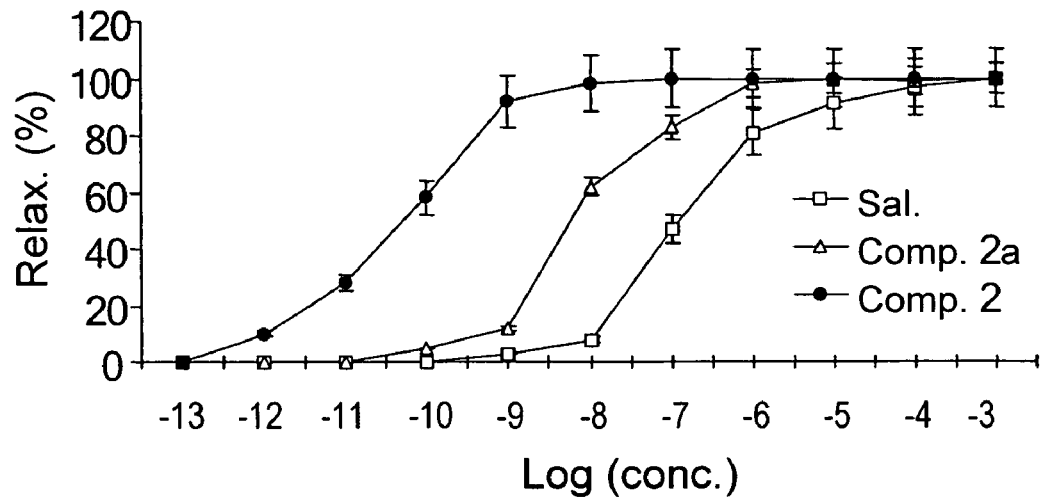
FIG. 1 shows the relaxation response (relax. %) of salbutamol (sal., open squares), compound 2 (comp. 2, filled circles) and its non-nitrosolated precursor, compound 2a (comp. 2a, open triangles) versus log of concentration (log (conc.)).

Provided are multifunctional β-agonist compounds for the treatment of respiratory disorders. The multifunctional β-agonist compound includes in one embodiment: a β-agonist component; an antioxidant, such as a reactive oxygen species scavenger; and a nitric oxide donor. Thus, in one embodiment, a β-agonist is provided in modified form and includes a reactive oxygen species (ROS) scavenger group and a nitric oxide donor group capable of releasing NO in a charged or neutral form. The β-agonist may be linked to at least one reactive oxygen species (ROS) scavenger and at least one nitric oxide donor. Exemplary β-agonists include salbutamol, salmetrol, fometeral, and terbutalin. The nitric oxide donors include —ONO, —ONO$_2$, —SNO and —NONOate. The antioxidant group, such as a ROS scavenger is, for example, a substituted nitroxide free radical; alkenyl group; aryl group; substituted aryl group, where the aryl group is substituted with, for example, —OH, —NH$_2$, —NHCHO or a NO donor group; or a group that is, or is capable of being converted in vivo into, a sulfhydryl in oxidized or reduced form.

The multifunctional β-agonist compounds, and compositions comprising the multifunctional β-agonist compounds, may be used in methods of treating respiratory disorders including asthma, bronchitis, emphysema, bronchospasms, pneumonia, bronchial hyper-reactivity, respiratory distress syndrome and other ailments in patients with obstructive airway or allergic disorders. The multifunctional β-agonist compounds, compositions comprising the multifunctional β-agonist compounds and methods described herein are also directed to avoiding adverse effects, development of tolerance (e.g. desensitization) or hypersensitivity on repeated administration. The multifunctional β-agonist compounds and compositions comprising the multifunctional β-agonist compounds as described herein may also be used in the manufacture of medicaments for the treatment of respiratory disorders.

The multifunctional β-agonist compounds, and compositions comprising the multifunctional β-agonist compounds, described herein not only provide a source of nitric oxide, which acts in the regulation of airway smooth muscle, but in acting as an antioxidant scavenger of superoxide anion and other reactive oxygen species give rise to both a direct benefit derived from removal of injurious superoxide anion and other reactive oxygen species and a benefit in protecting both ambient and endogenous and liberated exogenous NO from inactivation by superoxide anion and other reactive oxygen species.

As used herein, the term "multifunctional β-agonist compound" refers to a compound containing a β-agonist component, and additionally at least one NO donor component and at least one antioxidant component, such as an ROS scavenger component. The components may be linked, for example directly, indirectly and/or via a sharing of atoms, as described herein. The use of the term "multifunctional β-agonist compound" is not intended to necessarily require that the compound was formed by chemical modification of a β-agonist, since the synthesis would not necessarily involve a starting material that was a β-agonist that is further modified, and other routes of synthesis are contemplated. Rather, a "multifunctional β-agonist compound" is meant to be a molecule that not only includes a β-agonist component with β-agonist activity, but also the additional functionality of the NO donor and antioxidant (such as ROS scavenger) components. Thus, in one embodiment, multifunctional β-agonist compounds are provided that are β-agonists in a modified form wherein they include an NO donor group and a ROS scavenger group. It is to be understood that the compounds of the invention whether prepared from a β-agonist as a starting material or any other starting material retain their β-agonistic activity.

NO Donors

Groups that can act as nitric oxide donors are capable of acting as a source of nitric oxide (NO). The nitric oxide donor is, for example, an —ONO$_2$—ONO, —SNO or —NONOate group. In particular embodiments the NO donor is —ONO$_2$ or —SNO. The NO donor, for example, donates, transfers, or releases nitric oxide in either a neutral or a charged form. The nitric oxide donor may comprise any group capable of acting as a source of nitric oxide (NO) in a charged or uncharged form, including nitrosonium (NO$^+$), nitroxyl (NO$^-$) or nitric oxide (NO.).

Reactive Oxygen Species Scavengers

The multifunctional β-agonist compound may include an antioxidant group that can act as an antioxidant, preferably without reacting with nitric oxide, as well as the NO donor. The antioxidant group can be a reactive oxygen species (ROS) scavenger. As used herein, the term "reactive oxygen species (ROS) scavenger group" refers to a group capable of acting as a scavenger of, or reacting with, superoxide ($O_2^-$) or other reactive oxygen species (ROS) including hydroxyl radicals, peroxynitrite, hypochlorous acid and hydrogen peroxide. An antioxidant that preferentially scavenges, or reacts with, superoxide is termed a "superoxide dismutase mimic" ("SOD-mimic") or "superoxide dismutase mimetic"

("SOD-mimetic"). The reactive oxygen species superoxide ($O_2^-$), hydroxyl radicals, peroxynitrite, hypochlorous acid and hydrogen peroxide are considered biologically undesirable, while nitric oxide, as described above, may be biologically beneficial. Thus, the antioxidant or ROS scavenger group preferably does not react with, or scavenge, nitric oxide.

The multifunctional β-agonist compounds described herein may include one or more antioxidant or ROS scavenger groups. In some embodiments, the reactive oxygen species scavenger is a nitroxide free radical (NO.) group. In certain embodiments the compounds as described herein may comprise more than one ROS scavenger, for example at least one, at least two, at least three or at least four ROS scavenger groups.

As used herein, the ROS scavenger itself is not intended to be a group capable of donating nitric oxide (NO). Further, the ROS scavenger is provided in addition to the β-agonist component of the multifunctional β-agonist compound.

The antioxidant group, such as an ROS scavenger group, may be for example an alkenyl group; aryl group; substituted aryl group, where the aryl group is substituted with, for example, —OH, —$NH_2$, —NHCHO or a NO donor group; sulfhydryl or dithiol in oxidized or reduced form; or a group that is, or is capable of being converted in vivo into, a sulfhydryl in its oxidized or reduced form.

As used herein, the term "alkyl" includes branched or unbranched hydrocarbon chains, for example, including about 1 to about 18 carbons, or 1-15, or 1-10 or 1-5 carbons, such as methyl, ethyl, n-propyl, iso-propyl, n-butyl, sec-butyl, iso-butyl, tert.-butyl, octa-decyl and 2-methylpentyl. Alkyl may also include cyclic alkyl groups, for example, including about 5-8 carbons, such as cyclopentyl, cyclohexyl, cycloheptyl, or cyclooctyl. Alkyl can be optionally substituted with one or more functional groups such as hydroxyl, bromo, fluoro, chloro, iodo, mercapto or thio, cyano, alkylthio, aryl, carboxyl, carbalkoyl, alkenyl, nitro, amino, alkoxyl, amido, an NO donor group, and the like in the form of substituted alkyl. A cyclic alkyl group may be substituted with a straight or branched chain alkyl group.

The term "aryl" includes a chain of carbon atoms which form at least one aromatic ring having for example between about 6-14 carbon atoms, such as phenyl, naphthyl, anthracenyl and azulenyl.

The aryl optionally may be substituted with one or more functional groups such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, NO donor groups, and the like.

The term "heteroaryl" includes a ring system including one or more aromatic rings and containing one or more heteroatoms, N, O, or S, in the aromatic ring. Heteroaryl groups can be unsubstituted or may be substituted for example as described for alkyl and aryl groups. Examples of heteroaryl groups include, but are not limited to, pyridinyl, pyrazinyl, pyrimidinyl, benzothialozyl, pyrazolyl, benzoxazolyl, imidazolyl, pyrrolyl, thiadiazolyl, oxazolyl, isoxazolyl, pyridazinyl, triazolyl, thiazolyl, isothiazolyl, thiophenyl, furanyl, and quinolinyl.

In particular embodiments, the ROS scavenger may be a nitroxide free radical, wherein optionally the N is within a 3-, 4-, 5-, 6- or 7-membered ring, wherein the ring may be optionally substituted with, for example, straight or branched chain $C_1$-$C_3$ alkyl groups, alkoxy groups and groups capable of donating NO.

The nitroxide free radical is preferably substituted. In particular embodiments the nitroxide free radical is fully substituted at positions alpha to the nitroxide free radical, and may optionally be substituted at other positions on the ring. Exemplary substituents for the alpha positions include methyl or ethyl. Exemplary substituents for other ring positions include NO donor groups.

In certain other embodiments the substituted nitroxide free radical may also be substituted within the ring with an additional heteroatom, for example, —O— or —S—. (see structures Ia and Ib, below). Exemplary nitroxide free radicals include substituted pyrrolidinyloxy free radicals (e.g. PROXYL), substituted piperidinyloxy free radicals (e.g. TEMPO), substituted oxazolidinyloxy free radicals (e.g. DOXYL), oxazinyloxy free radicals, substituted thiazolidinyloxy free radicals and substituted thiazinyloxy free radicals.

In certain embodiments, the ROS scavenger(s) may be independently selected from the group consisting of substituted piperidinyloxy free radical, substituted 3-pyrrolidin-1-yloxy free radical, substituted oxazolidinyloxy free radical (e.g. DOXYL), and an optionally substituted lipoic acid moiety.

Examples of nitroxide free radical moieties which may be incorporated into the multifunctional β-agonist compounds include a 2,2,6,6-tetramethylpiperidinyloxy free radical (TEMPO) moiety (Ia, below, where X=C), a 2,2,5,5-tetramethyl-3-pyrrolidin-1-yloxy free radical (PROXYL) moiety (Ib, below, where X=C); 4,4-dimethyl-3-oxazolidinyloxy (DOXYL) free radical moiety, and a 2,2,4,4-tetramethyl-3-oxazolidinyloxy free radical moiety (Ib, below, where X=O). In structures Ia-f below, X is for example —S—, —C— or —O—. The nitroxide free radical moiety may be linked to the β-agonist moiety for example, directly, indirectly, via a linker (e.g. through an alkyl substituent group, see, for example Ic and Id), and/or via sharing of atoms, for example as shown in Formulas Ia-Ie or structures Ie and If below. The linkage may be to various carbon atoms on the ring, including those shown in structures Ic-If below.

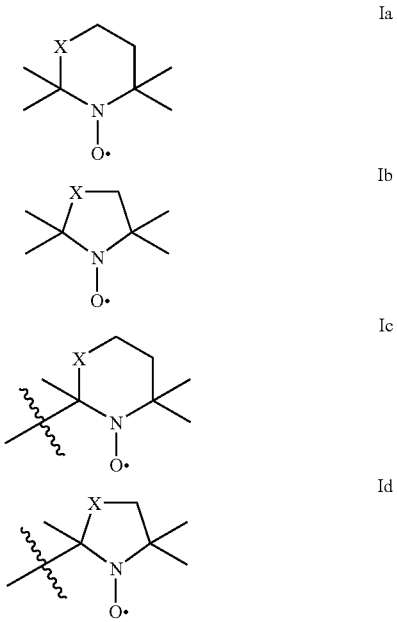

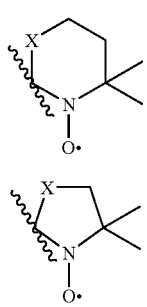

Ie

If

In other embodiments the ROS scavenger comprises a lipoic acid moiety or may be derived from the lipoic acid moiety. The lipoic acid moiety may be optionally substituted and is shown below:

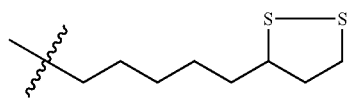

The lipoic acid moiety may be independently substituted by one or more groups such as straight or branched chain $C_1$-$C_{15}$ alkyl groups, $C_1$-$C_{15}$ alkoxy groups, hydroxy groups, amino groups ($NH_2$), —NHCHO groups, —$CH_2OH$ groups, and groups capable of donating NO in a charged or neutral form.

In other embodiments, the ROS scavenger may be a pantothenic acid SH-containing derived moiety as shown below, in either an oxidized or reduced form:

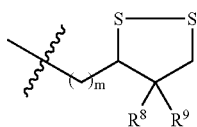

wherein, m is for example, 1-6, and $R^8$ and $R^9$ are for example each independently $C_1$-$C_3$ alkyl or H.

In other embodiments, the lipoic acid moiety may be modified by varying the length of the aliphatic chain connecting the heterocyclic ring to the β-agonist component of the multifunctional β-agonist compound. The chain may be for example $(CH_2)_n$ wherein n is an integer from 1-15. In certain embodiments n is 2-12, 5-12, or 8-12. In particular embodiments, n is 3 or 12 as shown below.

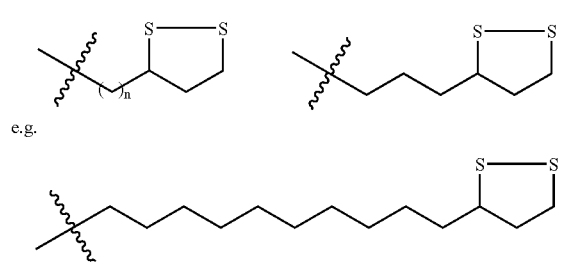

e.g.

In certain embodiments the ROS scavenger, including those described above, may be independently substituted with one or more alkyl groups such as $C_1$-$C_{15}$ alkyl groups, alkoxy such as $C_1$-$C_{15}$ alkoxy groups, hydroxy groups, amino groups including $NH_2$, —NHCHO groups, —$CH_2OH$ groups, and groups capable of donating NO in a charged or neutral form.

In other embodiments, the antioxidant may comprise or be one or more optionally substituted aryl groups or heteroaryl groups. In certain embodiments the aryl group is phenyl. The aryl groups may be optionally independently substituted by one or more groups including straight or branched chain $C_1$-$C_{15}$ alkyl groups, $C_1$-$C_{15}$ alkoxy groups, hydroxy groups, amino groups (such as $NH_2$), —NHCHO groups, —$CH_2OH$ groups, and groups capable of donating NO in a charged or neutral form.

In particular embodiments, the ROS scavenger group(s) comprises, one or more PROXYL moieties, one or more TEMPO moieties, one or more DOXYL moieties, one or more 2,2,4,4-tetramethyl-3-oxazolidinyloxy free radical moieties and/or one or more optionally substituted lipoic acid moieties. In particular embodiments the groups comprising N-oxide free radical moieties are independently substituted by one or more $C_1$-$C_3$ alkyl groups, for example methyl, ethyl or butyl, or one or more $C_1$-$C_3$ alkoxy groups.

The multifunctional β-agonist compounds may be modified to include one or more of the same or different antioxidant and/or ROS scavenger group.

β-Agonists

The β-agonist component of any of a variety of β-agonist compounds for the treatment of respiratory disorders can be present in the multifunctional β-agonist compounds. In one embodiment, a known β-agonist is provided in multifunctional form which further includes at least one NO donor and at least one ROS scavenger group. The β-agonist compound or component is one that is capable of exerting bronchorelaxation through stimulation of β-adrenoreceptors.

Exemplary β-agonists include compounds used in the treatment of respiratory disorders that are selective for the $β_2$ adrenergic receptors, such as terbutaline, albuterol, salbutamol, fenoterol, isoetharine, metaproterenol and, the so-called "long acting" selective $β_2$ sympathomimetic bronchodilator compounds formoterol, bambuterol and salmeterol. Another β-agonist is isoproterenol. A further class of β-agonists include the bronchorelaxants which are ephedrine derivatives, (e.g. albuterol, bambuterol, bitolterol, carbuterol, clenbuterol, clorprenaline, dioxethedrine, ephedfine, epinephrine, eprozinol, etafedrine, ethylnorepinephrine, fenoterol, formoterol, hexoprenaline, isoetharine, isoproterenol, mabuterol, metaproterenol, N-methylephedrine, pirbuterol, procaterol, protokylol, reproterol, rimiterol, salmeterol, soterenol, terbutaline, and tulobuterol).

Numerous $β_2$ sympathomimetic bronchorelaxant drugs are commercially available and clinically used, generally in pharmaceutically acceptable salt form, e.g., as the sulphate, hydrobromide, hydrochloride, fumarate or methanesulfonate or, where appropriate, one or other of the hydrate forms thereof. Beta agonists are useful as bronchodilator agents; they stimulate $β_2$ adrenergic receptors, increase intracellular cAMP, and inhibit the release of mast cell mediators, which can cause bronchoconstriction (Boushey, "Basic & Clinical Pharmacology" 7th Ed., pp. 118-151 and 325-342, Katzung, Ed. 1998, Appleton & Lange, Stamford, Conn.). Additional β-agonists used in the treatment of respiratory disorders are known in the art and may be used as described herein, for example, those described in "Sympathomimetic Enantiomers in the Treatment of Asthma" Ed. J. F. Costello (1997), Parthenon Publishing Group, Inc., London and "New Drugs for Asthma, Allergy and COPD", Ed. T. Hansel and P. J. Barnes (2001) Karger, London.

Albuterol acts selectively on $\beta_2$-adrenergic receptors to relax smooth muscle tissue, for example, in the bronchial system. Albuterol, also known as (alpha1-((tert.-butylamino)methyl)-4-hydroxy-m-xylene-alpha,alpha-diol) is commonly used to treat bronchial spasms associated with asthma and is the active component in well-known commercial bronchodilators such as Proventil™ and Ventolin™. Other formulations of albuterol include Aerolin™, salbulin, ventodisks, salbutamol, asmol, respax, respolin.

In certain examples the $\beta$-agonist compound or component elicits a bronchodilator effect, such as relief from the symptoms associated with obstructive airway diseases, which include but are not limited to respiratory distress, wheezing, coughing, shortness of breath, tightness or pressure in the chest and the like.

The problem of desensitization is particularly significant in the treatment of diseases involving bronchospasms, such as asthma, upon self-administration either orally or by aerosol of $\beta$-adrenergic agonists. Such $\beta$-agonists may be provided in a multifunctional form as disclosed herein.

Multifunctional $\beta$-Agonist Compounds

The multifunctional $\beta$-agonist compound may include an $\beta$-agonist component, and additionally, at least one NO-donor, and at least one antioxidant such as a reactive oxygen species (ROS) scavenger. The multifunctional $\beta$-agonist compound may include a $\beta$-agonist component linked to at least one NO-donor and at least one antioxidant. The term "linked" as used herein is intended to include direct and indirect linkages and shared atoms between any of the NO donor group, antioxidant, such as ROS scavenger group, and $\beta$-agonist component. The components may be linked in any order, for example, the ROS scavenger may be linked to both the NO donor and the $\beta$-agonist component, or the ROS scavenger may be linked only to the $\beta$-agonist component while the $\beta$-agonist component is also linked to the NO-donor (e.g. according to Formula 1).

Also included within the scope of the invention are salts of the compounds disclosed herein and stereoisomers thereof. The compounds of the present invention contain one or more asymmetric atoms and may exist in diastereomeric, racemic and optically active forms. All such compounds and compositions comprising these compounds are contemplated to be within the scope of this invention. Therefore, where a compound is chiral, the separate enantiomers, substantially free of the other, are included within the scope of the invention. Thus, one enantiomer may be in, for example, 95% or more purity. Further included are all mixtures of enantiomers or diastereomers.

Optically active forms of the compounds can be prepared using any method known in the art, including by resolution of the racemic form by recrystallization techniques, by chiral synthesis, extraction with chiral solvents, or by chromatographic separation using a chiral stationary phase. Examples of methods to obtain optically active materials include transport across chiral membranes, a technique whereby a racemate is placed in contact with a thin membrane barrier. The concentration or pressure differential causes preferential transport across the membrane barrier. Separation occurs as a result of the non-racemic chiral nature of the membrane which allows only one enantiomer of the racemate to pass through. Chiral chromatography, including simulated moving bed chromatography, is used in one embodiment. A wide variety of chiral stationary phases are commercially available.

Since superoxide anion is an available and continuously-formed by-product generated through normal metabolic processes, and since its elimination is mediated either by dismutation by the enzyme SOD or via its reaction with NO to form the potentially hazardous peroxynitrite, without being limited to any theory, the compounds are believed to be capable of simultaneously and favorably affecting both components; the NO and $O_2^-$. By virtue of the $\beta$-agonist activity, NO donation and superoxide scavenging properties being simultaneously delivered by the same molecule, the compounds of the present invention can increase the level of NO and reduce levels of superoxide thereby avoiding high levels of peroxynitrite and oxidant metabolites thereof and consequently increasing the effectiveness of the respiratory active agent.

In one embodiment, compounds of Formula 1, below, are provided:

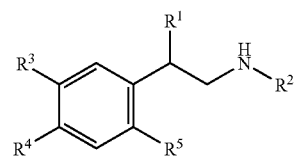

Formula 1 wherein $R^1$ is selected from the group consisting of —OH, —ONO, —ONO$_2$, —SNO, and —NONOate;

$R^2$ is alkyl or substituted alkyl, e.g., an optionally substituted straight or branched chain $C_1$-$C_{15}$ alkyl or optionally substituted $C_5$-$C_8$ cyclic alkyl;

or optionally $R^2$ is a an antioxidant group, such as an ROS scavenger;

or optionally $R^2$ is a group comprising an antioxidant, such as an ROS scavenger;

or optionally $R^2$ is a group comprising an NO donor and an antioxidant, such as an ROS scavenger, wherein optionally $R^2$ comprises a dithiol;

or optionally $R^2$ is a straight chain, branched or cyclic alkyl group substituted with an antioxidant, such as an ROS scavenger, such as a nitroxide free radical; or a straight chain, branched or cyclic alkyl group substituted with an NO donor; or a straight chain, branched or cyclic alkyl group substituted with an NO donor and an antioxidant, such as an ROS scavenger; or a straight chain, branched or cyclic alkyl group substituted with an NO donor and at least one aryl or heteroaryl group; or a cyclic alkyl group substituted with a straight or branched chain alkyl group and/or an NO donor;

or optionally $R^2$ is, or is a group comprising: an alkenyl group; substituted alkenyl group; aryl group; or substituted aryl group, where the aryl or alkenyl group is substituted with, for example, —OH, —NH$_2$, —NHCHO or an NO donor group;

or optionally $R^2$ is a group comprising a dithiol, for example, $R^2$ is a straight chain, branched or cyclic alkyl group substituted with a dithiol;

$R^3$ and $R^4$ are independently selected from the group consisting of —OH, —CH$_2$OH, —NH$_2$, and —NHCHO; or $R^3$ and $R^4$ together form an antioxidant, such as an ROS scavenger, such as a substituted N-oxide free radical, such as a substituted pyrrolidine N-oxide free radical, substituted piperidine N-oxide free radical, substituted oxazolidine N-oxide free radical, substituted oxazine N-oxide free radical, substituted thiazole N-oxide free radical, or substituted thiazine N-oxide free radical; or form amino or hydroxy protecting groups (e.g. N-formyl, acetal or ketal);

$R^5$ is selected from the group consisting of —H, —OH, —CH$_2$OH, —NH$_2$, —NHCHO, straight or branched chain C$_1$-C$_{15}$ alkyl, or straight or branched chain C$_1$-C$_{15}$ alkoxy; and wherein, in a preferred embodiment, the compound includes at least one ROS scavenger and at least one NO-donor (for example independently present on any one or more of $R^{1-4}$).

In another embodiment of Formula 1:

$R^1$ is —ONO$_2$, or —SNO;

$R^2$ is optionally substituted alkyl, e.g., optionally substituted linear or branched chain C$_1$-C$_{15}$ alkyl, or optionally substituted C$_5$-C$_8$ cyclic alkyl; or optionally substituted aryl, optionally substituted heteroaryl, a group comprising a substituted pyrrolidine N-oxide free radical or substituted piperidine N-oxide free radical, or a group that is, or may be converted in vivo to, a sulfhydryl in its oxidized or reduced form, or optionally $R^2$ is, or is a group comprising: an alkenyl group; substituted alkenyl group; aryl group; or substituted aryl group, where the aryl or alkenyl group is substituted with, for example, —OH, —NH$_2$, —NHCHO or an NO donor group;

wherein $R^2$ is optionally substituted with one or more groups such as, C$_1$-C$_3$ alkyl groups, C$_1$-C$_3$ alkoxy groups, —ONO, —ONO$_2$, —SNO, aryl, and antioxidant groups; and $R^3$ and $R^4$ are independently —OH, —CH$_2$OH, —NH$_2$, or —NHCHO; or together form an optionally substituted nitroxide radical, such as substituted pyrrolidine N-oxide free radical, substituted oxazolidine N-oxide free radical, or substituted piperidine N-oxide free radical or amino or hydroxy protecting groups; and $R^5$ is selected from the group consisting of —H, —OH, —CH$_2$OH, —NH$_2$, —NHCHO, straight or branched chain C$_1$-C$_{15}$ alkyl, or straight or branched chain C$_1$-C$_{15}$ alkoxy; and wherein, in a preferred embodiment, the compound includes at least one ROS scavenger and at least one NO donor.

Exemplary ROS scavenger and antioxidant groups include those as described herein such as groups which incorporate the lipoic acid moiety, or N-oxide free radical moiety, such as for example, substituted pyrrolidine, piperidine and oxazolidine N-oxide free radicals, and optionally substituted aryl groups as well as groups which are, or can be converted in vivo to, sulfyhydryl.

Exemplary substituted pyrrolidine N-oxide, substituted oxazine N-oxide or piperidine N-oxide free radicals which can be formed from $R^3$ and $R^4$ are shown in Formulas 1a-1e below, where $R^1$, $R^2$ and $R^5$ are for example as described herein: Thiazole, thiazine and oxazolidine N-oxide free radical analogues of Formulae 1a-1e are also contemplated.

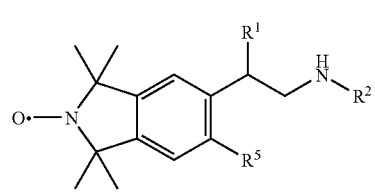

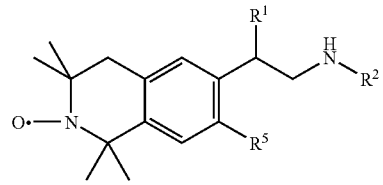

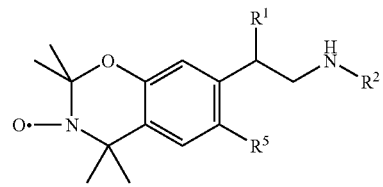

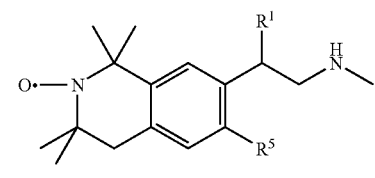

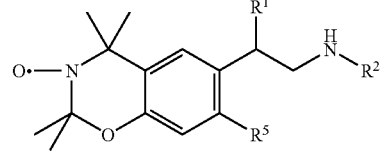

In some embodiments, compounds of Formula 2 are provided, as shown below:

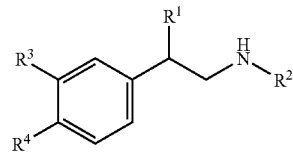

Formula 2 wherein $R^1$ is selected from the group consisting of —OH, —ONO, —ONO$_2$, —SNO, and —NONOate;

$R^2$ is alkyl or substituted alkyl, e.g., an optionally substituted straight or branched chain C$_1$-C$_{15}$ alkyl or optionally substituted C$_5$-C$_8$ cyclic alkyl;

or optionally $R^2$ is an antioxidant group, such as an ROS scavenger;

or optionally $R^2$ is a group comprising an antioxidant, such as an ROS scavenger; or a group comprising an NO donor and an antioxidant, such as an ROS scavenger, wherein optionally $R^2$ comprises a dithiol;

or optionally $R^2$ is a straight chain, branched or cyclic alkyl group substituted with an antioxidant, such as an ROS scavenger, such as a nitroxide free radical; or a straight chain, branched or cyclic alkyl group substituted with an NO donor; or a straight chain, branched or cyclic alkyl group substituted with an NO donor and an antioxidant, such as an ROS scavenger; or a cyclic alkyl group substituted with a straight or branched chain alkyl group and/or an NO donor, or a straight chain, branched or cyclic alkyl group substituted with an NO donor and at least one aryl or heteroaryl group; or a cyclic alkyl group substituted with a straight or branched chain alkyl group and/or an NO donor, or optionally $R^2$ is, or is a group comprising: an alkenyl group; substituted alkenyl group; aryl group; or substituted aryl group, where the aryl or alkenyl group is substituted with, for example, —OH, —NH$_2$, —NHCHO or an NO donor group;

or optionally $R^2$ is a group comprising a dithiol, such as a straight chain, branched or cyclic alkyl group substituted with a dithiol;

$R^3$ and $R^4$ are independently selected from the group consisting of —OH, CH$_2$OH, —NH$_2$, and —NHCHO; or $R^3$ and $R^4$ together form an antioxidant, such as an ROS scavenger, such as a substituted N-oxide free radical, such as a substituted pyrrolidine N-oxide free radical, substituted piperidine N-oxide free radical, substituted oxazolidine N-oxide free radical, substituted oxazine N-oxide free radical, substituted thiazole N-oxide free radical, or substituted thiazine N-oxide free radical; or form amino or hydroxy protecting groups (e.g. N-formyl, acetal or ketal);

wherein the N-oxide free radical may be substituted with one or more, groups independently selected C$_1$-C$_3$ alkyl groups and C$_1$-C$_3$ alkoxy groups, wherein, in a preferred embodiment, the compound includes at least one ROS scavenger and at least one NO donor.

In certain embodiments of Formula 2, $R^1$ is selected from the group consisting of —OH, —ONO, —ONO$_2$, —SNO, and —NONOate;

$R^2$ is an optionally substituted alkyl such as an optionally substituted straight or branched chain C$_1$-C$_{15}$ alkyl group or optionally substituted C$_5$-C$_8$ cyclic alkyl group, a group comprising an ROS scavenger, or a group comprising an ROS scavenger and/or an NO-donor;

wherein $R^2$ may be optionally substituted with, e.g., alkyl such as C$_1$-C$_3$ alkyl groups; or alkoxy, such as C$_1$-C$_3$ alkoxy groups; aryl; NO donor groups; or a lipoic acid moiety;

$R^3$ and $R^4$ are independently selected from the group consisting of —OH, —CH$_2$OH, —NH$_2$, and —NHCHO; or $R^3$ and $R^4$ together form a substituted N-oxide free radical, such as a substituted pyrrolidine N-oxide free radical, substituted oxazolidine N-oxide free radical, or a substituted piperidine N-oxide free radical;

wherein the N-oxide free radical may be substituted with one or more groups independently selected C$_1$-C$_3$ alkyl groups and C$_1$-C$_3$ alkoxy groups;

wherein, in a preferred embodiment, the compound includes at least one ROS scavenger and at least one NO donor.

In certain embodiments of Formula 1 or Formula 2 at least one of $R^1$, $R^2$, $R^3$ or $R^4$ comprises at least one ROS scavenger; and at least one of $R^1$, $R^2$, $R^3$ and $R^4$ comprises at least one NO donor.

In another embodiment of Formula 1 or 2:

$R^1$ is —ONO$_2$, or —SNO;

$R^2$ is optionally substituted alkyl, optionally substituted aryl, optionally substituted heteroaryl, substituted pyrrolidine N-oxide free radical, substituted oxazolidine free radical or substituted piperidine N-oxide free radical, or a group that is, or may be converted in vivo to, a sulfhydryl in its oxidized or reduced form, for example a dithiol;

wherein $R^2$ is optionally substituted with one or more groups such as C$_1$-C$_3$ alkyl groups, C$_1$-C$_3$ alkoxy groups, —ONO, —ONO$_2$, —SNO, aryl, and antioxidant groups; and $R^3$ and $R^4$ are independently —OH, —CH$_2$OH, —NH$_2$, or —NHCHO; or together form a group comprising a substituted nitroxide radical or amino or hydroxy protecting groups;

wherein the nitroxide may be substituted with one or more independently selected C$_1$-C$_3$ alkyl groups or C$_1$-C$_3$ alkoxy groups;

wherein, in a preferred embodiment, the compound includes at least one ROS scavenger and at least one NO donor.

In certain embodiments of Formula 1 and Formula 2, $R^1$, $R^2$, $R^3$, $R^4$ and $R^5$, are one of the embodiments as defined herein, and the compound includes at least one ROS scavenger and at least one NO donor.

In certain embodiments, $R^2$ comprises one or more substituted pyrrolidine, oxazolidine, oxazine, thiazole, thiazine or piperidine N-oxide free radicals, aryl moieties, or heteroaryl moieties, wherein the N-oxide, aryl and heteroaryl moieties may be independently substituted by one or more of the following groups, including one or more C$_1$-C$_{15}$ alkyl groups, C$_5$-C$_8$ cyclic alkyl groups, C$_1$-C$_{15}$ alkoxy groups, hydroxy groups, amino groups (NH$_2$), —NHCHO groups, —CH$_2$OH groups, or NO donor groups, such as —ONO, —ONO$_2$ or —SNO.

In another embodiment of Formula 1 or Formula 2, $R^2$ may be or comprise an antioxidant such as an ROS scavenger which optionally further includes an NO donor. The antioxidant group is e.g., an alkenyl group; aryl group; substituted aryl group, where the aryl group is substituted with, for example, —OH, —NH$_2$, —NHCHO or a NO donor group. In another embodiment, the antioxidant group is, e.g., heteroaryl, dithiol, substituted pyrrolidine, substituted oxazolidine, substituted oxazine, substituted thiazole, substituted thiazine or substituted piperidine N-oxide free radical moiety, or a lipoic acid moiety. In some embodiments, the lipoic acid moiety is substituted with one or more —OH, —ONO, —ONO$_2$, or —SNO groups. In particular embodiments, $R^2$ is an aliphatic (CH$_2$)$_p$ linker further attached to a reactive oxygen species scavenger group, wherein p is an integer between 2 and 12, e.g. 2-6, 6-8, 8-12, and wherein the linker is optionally substituted by one or more of the following groups such as alkyl including C$_1$-C$_{15}$ alkyl, C$_1$-C$_{15}$ alkoxy, hydroxy, amino, —NHCHO, —CH$_2$OH, aryl or an NO donor group such as —ONO, —ONO$_2$, and —SNO. $R^2$ also may be an ROS scavenger and NO donor group connected by an aliphatic linker (CH$_2$)$_p$.

In one embodiment of Formula 1 and Formula 2:

at least one of $R^1$, $R^2$, $R^3$ or $R^4$ comprises at least one ROS scavenger group;

at least one of $R^1$, $R^2$, $R^3$ or $R^4$ comprises at least one NO donor.

In another embodiment, where there is more than one NO donor group, the NO donor groups are the same.

In one embodiment of Formula 1, $R^1$ is selected from the group consisting of —OH, —ONO$_2$, and —SNO, $R^2$ is optionally substituted alkyl, such as linear, or branched chain C$_1$-C$_{15}$ alkyl or C$_5$-C$_8$ cyclic alkyl; including, an alkyl group substituted with a substituted pyrrolidine, substituted oxazolidine or substituted piperidine N-oxide free radical; an alkyl group substituted with one or more aryl or heteroaryl groups; or an alkyl group substituted with a group that is, or may be converted in vivo to, a sulfhydryl in its oxidized or reduced form, such as, for example, a dithiol or a lipoic acid moiety;

wherein $R^2$ may be additionally optionally substituted with one or more independently selected groups including $C_1$-$C_3$ alkyl groups, $C_1$-$C_3$ alkoxy groups, —$ONO_2$, or —SNO;

$R^3$ and $R^4$ are independently —OH; —$CH_2OH$; —$NH_2$; —NHCHO; or $R^3$ and $R^4$ together form a substituted pyrrolidine, substituted oxazolidine, substituted oxazine, substituted thiazole, substituted thiazine or substituted piperidine N-oxide free radical, or together form an amino or hydroxy protecting group (e.g. N-formyl, acetal or ketal); wherein the N-oxide free radical is optionally substituted with one or more groups independently selected from $C_1$-$C_3$ alkyl groups and $C_1$-$C_3$ alkoxy groups; and $R^5$ is selected from the group consisting of —H, —OH, —$CH_2OH$, —$NH_2$, —NHCHO, and straight or branched chain $C_1$-$C_3$ alkyl, straight or branched chain $C_1$-$C_3$ alkoxy.

In another embodiment of Formula 1, $R^1$ is —$ONO_2$ or —SNO;

$R^2$ is optionally substituted alkyl, such as linear or branched chain $C_1$-$C_{15}$ alkyl, or optionally substituted $C_5$-$C_8$ cyclic alkyl; a substituted pyrrolidine, substituted oxazolidine or substituted piperidine N-oxide free radical; an alkyl group substituted with an aryl or heteroaryl group; an alkyl group substituted with an N-oxide free radical, such as substituted pyrrolidine, substituted oxazolidine or substituted piperidine N-oxide free radical; or a group that is, or may be converted in vivo to, a sulfhydryl in its oxidized or reduced form, such as a dithiol or lipoic acid moiety;

wherein $R^2$ may be optionally substituted with —$ONO_2$, or —SNO;

$R^3$ and $R^4$ together form a substituted pyrrolidine, or substituted piperidine nitroxide free radical, or form amino or hydroxy protecting groups (e.g. N-formyl, acetal or ketal); and $R^5$ is selected from the group consisting of H, —OH, —$CH_2OH$, —$NH_2$, —NHCHO, and straight or branched chain $C_1$-$C_3$ alkyl, straight or branched chain $C_1$-$C_3$ alkoxy.

In another embodiment of Formula 1, $R^1$ is —OH, —$ONO_2$, or —SNO;

$R^2$ is or comprises an optionally substituted linear or branched chain $C_1$-$C_{15}$ alkyl group or an optionally substituted $C_5$-$C_8$ cyclic alkyl group; a substituted pyrrolidine or substituted piperidine N-oxide free radical; an alkyl group substituted with one or more aryl or heteroaryl group; or an alkyl group substituted with a group that is or may be converted in vivo to a sulfhydryl in its oxidized or reduced form;

wherein $R^2$ may be optionally substituted with one or more groups such as $C_1$-$C_3$ alkyl groups, $C_1$-$C_3$ alkoxy groups, —ONO, —$ONO_2$, or —SNO;

$R^3$ and $R^4$ are —OH, —$CH_2OH$, —NCHOH, or together form a substituted pyrrolidine or substituted piperidine N-oxide free radical; and $R^5$ is selected from the group consisting of —H, —OH, —$CH_2OH$, —$NH_2$, —NHCHO, straight or branched chain $C_1$-$C_3$ alkyl, and straight or branched chain $C_1$-$C_3$ alkoxy; and wherein in one preferred embodiment $R^5$ is —H.

In one embodiment, $R^2$ is:

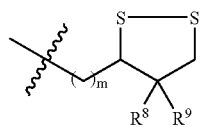

wherein m is 1-6 and $R^8$ and $R^9$ are independently $C_1$-$C_3$ alkyl or —H.

In another embodiment of Formula 1, $R^1$ is —$ONO_2$ or —SNO;

$R^2$ is optionally substituted alkyl such as linear or branched $C_1$-$C_{15}$ alkyl or optionally substituted $C_5$-$C_8$ cyclic alkyl; a group comprising substituted pyrrolidine or substituted piperidine N-oxide free radical;

or an alkyl group substituted with one or more aryl, heteroaryl, or dithiol group;

$R^3$ and $R^4$ together form a substituted pyrrolidine N-oxide free radical or a piperidine N-oxide free radical; and $R^5$ is —H.

In another embodiment of Formula 1, $R^1$ is —$ONO_2$;

$R^2$ is optionally substituted alkyl such as linear or branched chain $C_1$-$C_{15}$ alkyl; an alkyl group substituted with a substituted pyrrolidine or substituted piperidine N-oxide free radical; or an alkyl group substituted with one or more aryl, heteroaryl or dithiol groups;

$R^3$ and $R^4$ together form a substituted pyrrolidine or piperidine N-oxide free radical; and $R^5$ is —H.

In some embodiments of Formula 1 or 2, $R^2$ is alkyl such as t-butyl or is chosen from the following:

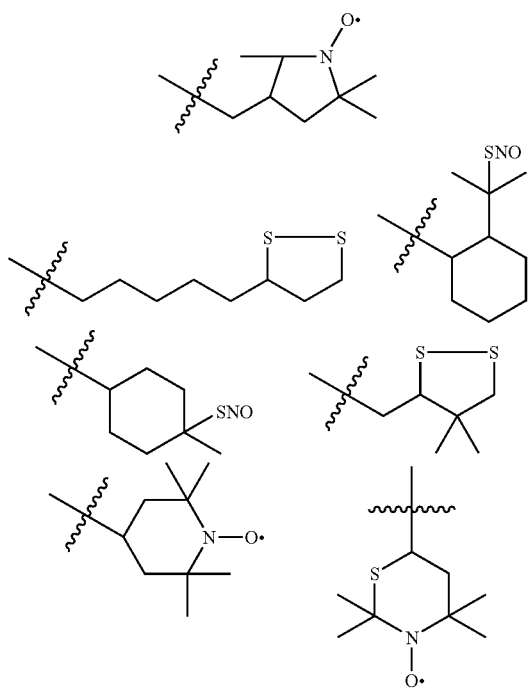

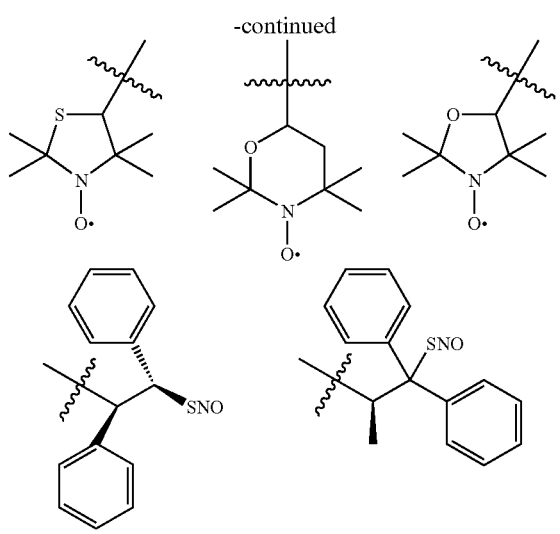

Figure 2:
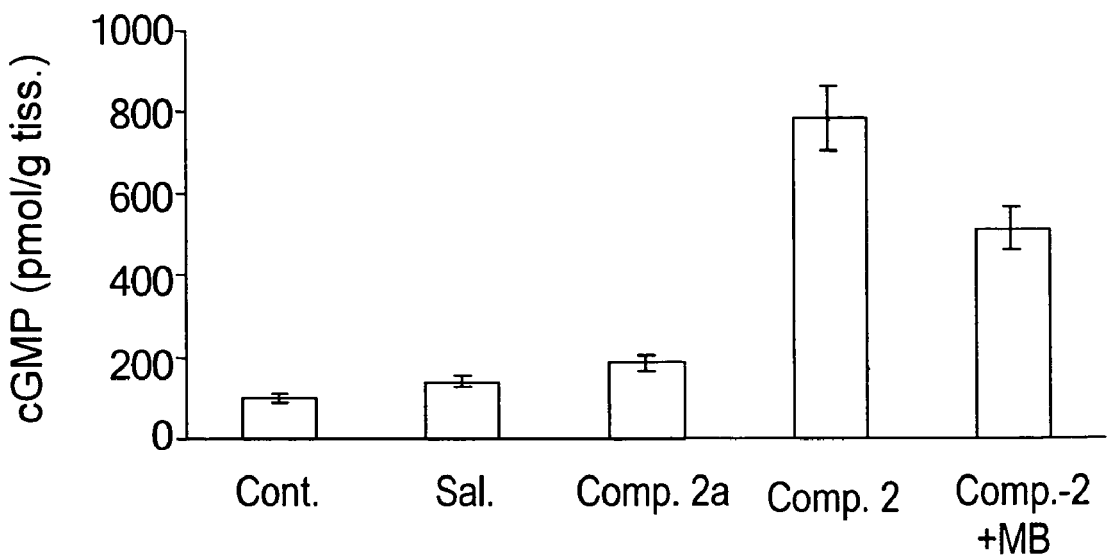
FIG. 2 shows the cGMP response of tracheal rings to a control (cont.), salbutamol, compound 2a (non-nitrosolated precursor of compound 2), compound 2, and compound 2 in the presence of methylene blue (MB).

Examples of multifunctional β-agonist compounds may be found in FIGS. 1 and 2. Examples of syntheses of such compounds may be found in Examples 1-10 and in the description herein.

In compounds of Formula 1 and 2, $R^1$ is selected from the group consisting of —OH, —ONO, —ONO$_2$, —SNO, and —NONOate. In a preferred embodiment, $R^1$ is selected from the group consisting of —OH, —ONO$_2$, and —SNO. In another preferred embodiment, $R^1$ is —ONO$_2$, or —SNO. In another preferred embodiment, $R^1$ is —ONO$_2$.

In compounds of Formula 1 and 2, in a preferred embodiment, $R^2$ is alkyl or substituted alkyl, e.g., an optionally substituted straight or branched chain $C_1$-$C_{15}$ alkyl; a group comprising an antioxidant, such as an ROS scavenger; or a group comprising an NO donor and an antioxidant, such as an ROS scavenger, wherein optionally $R^2$ comprises a dithiol.

In another preferred embodiment, $R^2$ is optionally substituted alkyl, e.g., optionally substituted linear or branched chain $C_1$-$C_{15}$ allyl, optionally substituted $C_5$-$C_8$ cyclic alkyl, optionally substituted aryl, optionally substituted heteroaryl, a group comprising a substituted pyrrolidine N-oxide free radical or substituted piperidine N-oxide free radical, or a group that is, or may be converted in vivo to, a sulfhydryl in its oxidized or reduced form, wherein $R^2$ is optionally substituted with one or more groups such as $C_1$-$C_3$ alkyl groups, $C_1$-$C_3$ alkoxy groups, —ONO, —ONO$_2$, —SNO, and an antioxidant group.

In another preferred embodiment, $R^2$ is an optionally substituted alkyl, such as an optionally substituted straight or branched chain $C_1$-$C_{15}$ alkyl group, or optionally substituted $C_5$-$C_8$ cyclic alkyl group; a group comprising an ROS scavenger; or a group comprising an ROS scavenger and/or an NO-donor; wherein $R^2$ may be optionally substituted with, e.g., alkyl, such as $C_1$-$C_3$ alkyl groups or alkoxy, such as $C_1$-$C_3$ alkoxy groups.

In another preferred embodiment, $R^2$ is optionally substituted alkyl, optionally substituted aryl, optionally substituted heteroaryl, a substituted pyrrolidine N-oxide free radical or substituted piperidine N-oxide free radical, or a group that is, or may be converted in vivo to, a sulfhydryl in its oxidized or reduced form; wherein $R^2$ may be optionally substituted with one or more groups independently selected from $C_1$-$C_3$ alkyl groups, $C_1$-$C_3$ alkoxy groups, —ONO, —ONO$_2$, or —SNO.

In another preferred embodiment, $R^2$ comprises one or more substituted pyrrolidine, oxazolidine, oxazine, thiazole, thiazine or piperidine N-oxide free radicals, aryl moieties, or heteroaryl moieties, wherein the N-oxide, aryl and heteroaryl moieties may be independently substituted by one or more of the following groups, including one or more $C_1$-$C_{15}$ alkyl groups, $C_5$-$C_8$ cyclic alkyl groups, $C_1$-$C_{15}$ alkoxy groups, hydroxy groups, amino groups (NH$_2$), —NHCHO groups, —CH$_2$OH groups, or NO donor groups, such as —ONO, —ONO$_2$ or —SNO.

In another preferred embodiment, $R^2$ comprises an antioxidant such as an ROS scavenger and optionally further comprises an NO donor. The antioxidant group is e.g., aryl, heteroaryl, dithiol, substituted pyrrolidine oxazolidine, oxazine, thiazole, thiazine or piperidine N-oxide free radical moiety, or a lipoic acid moiety. In some embodiments, the lipoic acid moiety is substituted with one or more —OH, —ONO, —ONO$_2$, or —SNO groups. In particular embodiments, $R^2$ is an aliphatic (CH$_2$)$_p$ linker further comprising a reactive oxygen species scavenger group, wherein p is an integer between 2 and 12, e.g. 2-6, 6-8, 8-12, and wherein the linker is optionally substituted by one or more of the following groups such as alkyl including $C_1$-$C_8$ alkyl, $C_1$-$C_8$ alkoxy, hydroxy, amino, —NHCHO, —CH$_2$OH, or an NO donor group such as —ONO, —ONO$_2$, and —SNO. $R^2$ also may comprise an ROS scavenger and NO donor group connected by an aliphatic linker (CH$_2$)$_p$.

In another preferred embodiment, $R^2$ is optionally substituted alkyl, such as, linear, or branched chain $C_1$-$C_{15}$ alkyl or $C_5$-$C_8$ cyclic alkyl; a group comprising a substituted pyrrolidine or substituted piperidine N-oxide free radical; a group comprising an aryl, heteroaryl group; or comprises a group that is, or may be converted in vivo to, a sulfhydryl in its oxidized or reduced form; wherein $R^2$ is optionally substituted with one or more independently selected groups including $C_1$-$C_3$ alkyl groups, $C_1$-$C_3$ alkoxy groups, —ONO$_2$, or —SNO.

In another preferred embodiment, $R^2$ is optionally substituted alkyl, such as linear or branched chain $C_1$-$C_{15}$ alkyl, or a group comprising an optionally substituted $C_5$-$C_8$ cyclic alkyl; a substituted pyrrolidine or substituted piperidine N-oxide free radical; a groups comprising an aryl or heteroaryl group; or a group that is, or may be converted in vivo to, a sulfhydryl in its oxidized or reduced form; wherein $R^2$ may be optionally substituted with —ONO$_2$, or —SNO.

In another preferred embodiment, $R^2$ comprises an optionally substituted linear or branched chain $C_1$-$C_{15}$ alkyl group or an optionally substituted $C_5$-$C_8$ cyclic alkyl groups; a substituted pyrrolidine or piperidine N-oxide free radical; a group comprising an aryl or heteroaryl group; or a group that is or may be converted in vivo to a sulfhydryl in its oxidized or reduced form; wherein $R^2$ may be optionally substituted with one or more groups such as $C_1$-$C_3$ alkyl groups, $C_1$-$C_3$ alkoxy groups, —ONO, —ONO$_2$, or —SNO.

In another preferred embodiment, $R^2$ is:

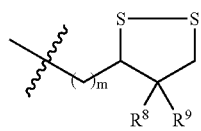

wherein m is 1-6 and $R^8$ and $R^9$ are independently $C_1$-$C_3$ alkyl or H.

In another preferred embodiment, $R^2$ is optionally substituted alkyl such as linear or branched $C_1$-$C_{15}$ alkyl or optionally substituted $C_5$-$C_8$ cyclic alkyl; a group comprising substituted pyrrolidine or substituted piperidine N-oxide free radical; or a group comprising an aryl, heteroaryl, or dithiol.

In another preferred embodiment, $R^2$ is optionally substituted alkyl such as linear or branched chain $C_1$-$C_{15}$ alkyl; a group comprising a substituted pyrrolidine or substituted piperidine N-oxide free radical; or a group comprising an aryl, heteroaryl or dithiol.

In compounds of Formula 1 and 2, $R^3$ and $R^4$ may be independently selected from the group consisting of —OH, —CH$_2$OH, —NH$_2$, and —NHCHO; or $R^3$ and $R^4$ together form an antioxidant, such as an ROS scavenger, such as a substituted N-oxide free radical, such as a substituted pyrrolidine N-oxide free radical, substituted piperidine N-oxide free radical, substituted oxazolidine N-oxide free radical, substituted oxazine N-oxide free radical, substituted thiazole N-oxide free radical, or substituted thiazine N-oxide free radical.

In a preferred embodiment, $R^3$ and $R^4$ are independently —OH, —CH$_2$OH, —NH$_2$, or —NHCHO; or together form an optionally substituted nitroxide radical, such as substituted pyrrolidine N-oxide free radical or substituted piperidine N-oxide free radical or amino or hydroxy protecting groups.

In another preferred embodiment, $R^3$ and $R^4$ are independently selected from the group consisting of —OH, —CH$_2$OH, —NH$_2$, and —NHCHO; or $R^3$ and $R^4$ together form a substituted N-oxide free radical, such as a substituted pyrrolidine N-oxide free radical, or a substituted piperidine N-oxide free radical; wherein the N-oxide free radical may be substituted with one or more groups independently selected $C_1$-$C_3$ alkyl groups and $C_1$-$C_3$ alkoxy groups.

In another preferred embodiment, $R^3$ and $R^4$ are independently —OH, —CH$_2$OH, —NH$_2$, or —NHCHO; or together form a group comprising a substituted nitroxide radical or amino or hydroxy protecting groups; wherein the nitroxide may be substituted with one or more independently selected $C_1$-$C_3$ alkyl groups or $C_1$-$C_3$ alkoxy groups.

In another preferred embodiment, $R^3$ and $R^4$ are independently —OH; —CH$_2$OH; —NH$_2$; —NHCHO; or $R^3$ and $R^4$ together form a substituted pyrrolidine or substituted pyrrolidine substituted oxazolidine, substituted oxazine, substituted thiazine or substituted piperidine N-oxide free radical, or together form an amino or hydroxy protecting group (e.g. N-formyl, acetal or ketal); wherein the N-oxide free radical is optionally substituted with one or more groups independently selected from $C_1$-$C_3$ alkyl groups and $C_1$-$C_3$ alkoxy groups.

In another preferred embodiment, $R^3$ and $R^4$ together form a substituted pyrrolidine or piperidine nitroxide radical, or form amino or hydroxy protecting groups (e.g. N-formyl, acetal or ketal).

In another preferred embodiment, $R^3$ and $R^4$ are —OH, —CH$_2$OH, —NCHOH, or together form a substituted pyrrolidine or substituted piperidine N-oxide free radical.

In another preferred embodiment, $R^3$ and $R^4$ together form a substituted pyrrolidine N-oxide free radical or a substituted piperidine N-oxide free radical. In compounds of Formula 1, $R^5$ is selected from the group consisting of —H, —OH, —CH$_2$OH, —NH$_2$, —NHCHO, straight or branched chain $C_1$-$C_{15}$ alkyl, or straight or branched chain $C_1$-$C_{15}$ alkoxy.

In another preferred embodiment, $R^5$ is selected from the group consisting of —H, —OH, —CH$_2$OH, —NH$_2$, —NHCHO, and straight or branched chain $C_1$-$C_3$ alkyl, straight or branched chain $C_1$-$C_3$ alkoxy.

In another preferred embodiment, $R^5$ is —H.

In compounds of Formula 1 and 2, in a preferred embodiment, at least one of $R^1$, $R^2$, $R^3$ or $R^4$ comprises at least one ROS scavenger.

In another preferred embodiment, at least one of $R^1$, $R^2$, $R^3$ or $R^4$ comprises at least one NO donor.

In another preferred embodiment, the compound includes at least one ROS scavenger and at least one NO donor.

In another preferred embodiment, each of $R^1$, $R^2$, $R^3$, $R^4$ and $R^5$ are selected the embodiments as defined herein, and the compound includes at least one ROS scavenger and at least one NO donor.

In another preferred embodiment, each of $R^1$, $R^2$, $R^3$, $R^4$ and $R^5$ are selected from the embodiments as defined herein.

In another preferred embodiment, where there is more than one NO donor, the NO donor groups are the same.

Synthesis of Multifunctional β-Agonist Compounds

Multifunctional β-agonist compounds may be synthesized as described herein using methods available in the art and standard techniques in organic chemistry, as described, for example, in *March's Advanced Organic Chemistry: Reactions, Mechanisms, and Structure*, 5th Edition (2000) M. B. Smith & J. March, John Wiley & Sons, New York, New York; *Organic Chemistry* 6$^{th}$ Ed. (1992) R. Morrison & R. Boyd, Benjamin Cummings, San Francisco. Synthetic methods such as these are known in the art and are further described in Hett et al. (1994) *Tetrahedron Letters* 35(50): 9375-9378 and Hett et al. (1997) *Tetrahedron Letters* 38(7): 1125-1128.

Examples of multifunctional β-agonist compounds are compounds 1-10 shown in FIGS. 1 and 2, while the details of their synthesis are described in Examples 1-10.

The general approach for synthesis of compounds of the general formula I is outlined in Scheme 1 below:

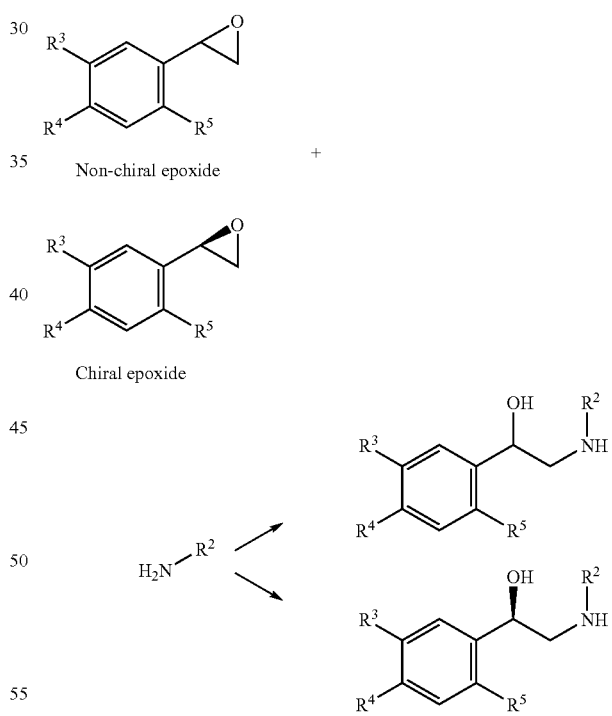

The starting materials, H$_2$NR$^2$, are chiral or non-chiral amines, usually in the N-benzylated form. Synthetic methods such as these are known in the art and are further described in Hett et al. (1994) *Tetrahedron Letters* 35(50): 9375-9378 and Hett et al. (1997) *Tetrahedron Letters* 38(7): 1125-1128.

A more detailed reaction scheme for the synthesis of the non-chiral and chiral epoxides is shown below in Scheme 2. In cases where the aryl ring of the β-agonist constitutes itself a ROS scavenger group (e.g., 1,1,3,3-tetramethylisoindolin- 2-yloxyl free radical), the chiral/non-chiral epoxides are synthesized as shown in detail in Scheme 3 below.

Scheme 2

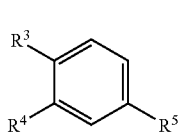 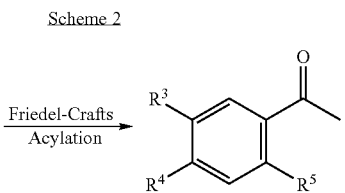

Diprotected Salicylic acid or salicyl alcohol

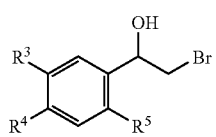 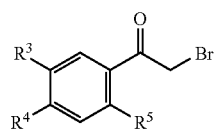

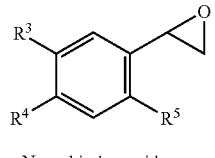 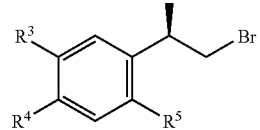

Non-chiral epoxide

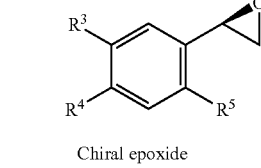

Chiral epoxide

Scheme 3

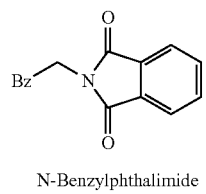 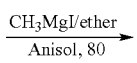 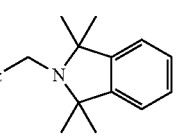

N-Benzylphthalimide

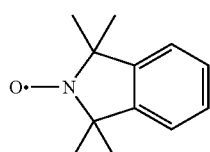

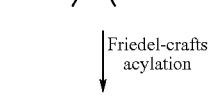

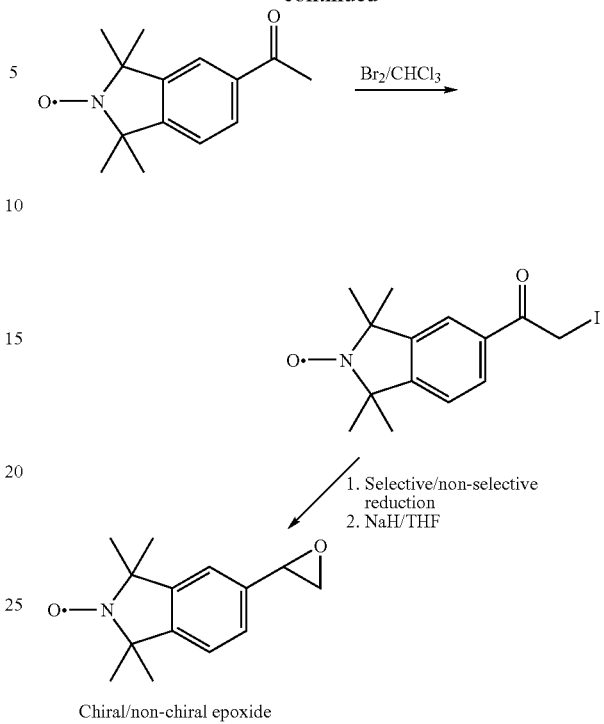

Chiral/non-chiral epoxide

Scheme 3, above, depicts the synthesis of a non-chiral epoxide incorporating a stable nitroxide radical containing a 5-membered ring (PROXYL moiety).

Methods of bromination of acetophenone derivatives are available in the art, such as bromination with $Br_2$ and bromination with pyrrolidinone hydrotribromide.

Respiratory Disorders

The present invention provides the compounds of the present invention for use in therapy.

The present invention further provides use of the compounds of the present invention in the manufacture of a medicament for the treatment of respiratory disorders.

The multifunctional β-agonist compounds are useful in treating a variety of respiratory disorders. Respiratory disorders include asthma, chronic bronchitis, bronchiectasis and emphysema, Chronic Obstructive Pulmonary Diseases (COPDs) or Chronic Obstructive Airway Disease (COADs).

COPDs are often characterized as being accompanied by chronic or recurrent obstruction to air flow within the lung. Increased resistance to air flow may result from narrowing or restriction of an airway at any level, including partial or complete obstruction from the trachea and larger bronchi to the terminal and respiratory bronchioles.

Another major class of pulmonary or respiratory diseases are often referred to as restrictive diseases, which maybe characterized by reduced expansion of lung parenchyma, with a reduced total lung capacity. Many pathologic conditions associated with respiratory disorders have both obstructive and restrictive components (Cotran et al., "Robbins Pathologic Basis of Disease" 4th Ed. 1989, W.B. Saunders Co., Philadelphia, Pa., pp 755-797).

Asthma may be characterized as an obstructive respiratory disorder characterized by increased responsiveness of the airway to various stimuli, which may potentiate spasmic constriction of the bronchial airways. Asthma can occur secondarily to a variety of stimuli (Cotran et al., "Robbins Pathologic Basis of Disease" 4th Ed. 1989, W.B. Saunders Co., Philadelphia, Pa., pp 755-797). Chronic asthma can also be considered to be predominantly an inflammatory disease with associated bronchospasm. The degree of reactivity and narrowing of the bronchi in response to stimuli is greater in asthmatics than in normal individuals. Persistent inflammation may be responsible for the bronchial hyperreactivity or airway hyperresponsiveness (AHR). Mucosal edema, mucus plugging and hypersecretion XXcan be also present; and pulmonary parenchyma can be common. Asthmatics manifesting such imbalance usually have hyperactive bronchi and, even without symptoms, bronchoconstriction may be present. Overt asthma attacks may occur when such individuals are subjected to various stresses, such as viral respiratory infection, exercise, emotional upset, nonspecific factors (e.g., changes in barometric pressure or temperature), inhalation of cold air or irritants (e.g., gasoline fumes, fresh paint and noxious odors, or cigarette smoke), exposure to specific allergens, and ingestion of aspirin or sulfites in sensitive individuals. Asthma is often characterized as "extrinsic" or "allergic", where the asthmatic episode is precipitated by allergens (e.g. most commonly airborne pollens and molds, house dust, animal danders) or "nonallergic" or "intrinsic", where symptomatic episodes seem to be triggered by non-allergenic factors (e.g. infection, irritants, emotional factors). In some individuals both allergenic and non-allergenic factors may be significant The compounds described herein can be used in the treatment of intrinsic and extrinsic asthma. They are especially applicable to the treatment of allergy or atopic (e.g. IgE-mediated) asthma or non-atopic asthma, as well as exercise induced asthma, occupational asthma, asthma induced following bacterial infection or drug, e.g. aspirin, ingestion and other non-allergic asthmas. The multifunctional β-agonist compounds may also be used in the treatment and/or prophylaxis of respiratory conditions such as chronic obstructive pulmonary or airways disease (COPD or COAD), chronic bronchitis, emphysema, respiratory distress syndrome (in child or adult), pneumonia, bronchial hyperreactivity, bronchiectasis, and airway hyperresponsiveness (AHR).

Asthma is often categorized as atopic (allergic), nonreaginic (where precipitating factor is a respiratory infection), pharmacologic (e.g. aspirin-sensitive or other drug sensitivity), occupational (e.g. chemical challenge from environmental stimuli), allergic bronchopolumonary aspergillosis (antigen challenge (e.g. spores)) (Cotran et al., "Robbins Pathologic Basis of Disease" 4th Ed. 1989, W.B. Saunders Co., Philadelphia, Pa., pp 755-797). The multifunctional β-agonist compounds discussed herein may be used in the treatment of each of these conditions or where combinations of factors are responsible for the clinical manifestation of the disorder.

Chronic bronchitis is a condition often associated with prolonged exposure to bronchial irritants and accompanied by mucus hypersecretion and certain structural changes in the bronchi. Usually associated with cigarette smoking, it is characterized clinically by chronic productive cough. Chronic obstructive bronchitis is often characterized as chronic bronchitis associated with extensive alterations of the small airways leading to clinically significant airways obstruction (Cotran et al., "Robbins Pathologic Basis of Disease" 4th Ed. 1989, W.B. Saunders Co., Philadelphia, Pa., pp 755-797).

The present invention is especially applicable in the treatment of respiratory conditions including, but not limited to, the respiratory disorders disclosed herein. As used herein, and as well-understood in the art, "treatment" is an approach for obtaining beneficial or desired results, including clinical results. For purposes of this invention, beneficial or desired clinical results can include one or more, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

The present invention is applicable in the treatment of severe acute respiratory syndrome (SARS). The current treatment protocol for this, most probably viral, disorder, is mainly supportive, and entails administration of oxygen and β-agonists.

Preferred are compounds that are potent and can be administered locally at very low doses, thus avoiding systemic adverse effects. Compounds also are preferred that possess both cAMP and cGMP stimulating activity via simultaneous activation of adenylyl cyclase and guanylyl cyclase, respectively. Also preferred are compounds with potent antioxidant characteristics and concurrent potent mucolytic properties. The multifunctional β-agonist compounds with anti-ROS activity and NO donor properties can exert a significant impact on the severity, control, and the natural course of respiratory diseases involving oxidative stress and free radical injury. Because of their multi-mechanistic actions, tolerance to their broncho-protective effect can preferably be avoided. The absence of tolerance can avoid the necessity of medium- to high-dose steroid therapy. The development of tolerance is disadvantageous since when administering a composition or drug in repeated dosage or over a period of time, the amount of the composition or the frequency of administration of the drug or composition given to the patient must be increased in order to achieve the same effect as the lower dosage given at an earlier time point in the course of treatment.

Formulations and Dosage

The compounds can be provided in a variety of formulations and dosages. The compounds may be provided in a pharmaceutically acceptable form and/or in a salt form.

In one embodiment, the compounds are provided as non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the multifunctional β-agonist compounds and salts thereof, for example, hydrates.

The multifunctional β-agonist compounds may have one or more asymmetric centres, and may accordingly exist both as enantiomers and as diastereoisomers. It is to be understood that all such isomers and mixtures thereof are encompassed within the scope of the present invention.

The multifunctional β-agonist compounds may be administered by oral, parenteral (e.g., intramuscular, intraperitoneal, intravenous, ICV, intracisternal injection or infusion, subcutaneous injection, or implant), buccal, by inhalation spray, nasal, vaginal, rectal, sublingual, or topical routes of administration and may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds of the invention may be effective in humans.

The pharmaceutical compositions for the administration of the multifunctional β-agonist compounds may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired therapeutic effect.

The pharmaceutical compositions containing the multifunctional β-agonist compound as active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. The multifunctional β-agonist compounds may also be administered in the form of suppositories for rectal administration of the drug.

For topical use, creams, ointments, jellies, solutions or suspensions, etc., containing the multifunctional β-agonist compounds may be employed.

According to the present invention, multifunctional β-agonist compounds can be delivered by any of a variety of inhalation devices and methods known in the art, including, for example: U.S. Pat. No. 6,241,969; U.S. Pat. No. 6,060,069; U.S. Pat. No. 6,238,647; Hughes et al., U.S. Pat. No 6,335,316; Rubsamen; U.S. Pat. No. 5,364,838; Rubsamen, U.S. Pat. No. 5,672,581; Platz, et al., WO96/32149; Patton, et al., WO95/24183; Johnson, et al., U.S. Pat. No. 5,654,007; Goodman, et al., U.S. Pat. No. 5,404,871; Rubsamen, et al., U.S. Pat. No. 5,672,581; Gonda, et al., U.S. Pat. No. 5,743,250; Rubsamen, U.S. Pat. No. 5,419,315; Rubsamen, et al., U.S. Pat. No. 5,558,085; Gonda, et al., WO98/33480; Rubsamen, U.S. Pat. No. 5,364,833; Laube, et al., U.S. Pat. No. 5,320,094; Eljamal, et al. U.S. Pat. No. 5,780,014; Backstrom, et al., U.S. Pat. No. 5,658,878; Backstrom, et al., 5,518,998; Backstrom, et al., 5,506,203; Meezan, et al., U.S. Pat. No. 5,661,130; Hodson, et al., U.S. Pat. No. 5,655,523; Schultz, et al., U.S. Pat. No. 5,645,051; Eisele, et al., U.S. Pat. No. 5,622,166; Mecikalski, et al., U.S. Pat. No. 5,577,497; Mecikalski, et al., U.S. Pat. No. 5,492,112; Williams, et al., U.S. Pat. No. 5,327,883; Williams, U.S. Pat. No. 5,277,195; U.S. patent application No. 20010041190; U.S. patent application No. 20020006901; and U.S. patent application No.20020034477.

Included among the devices which may be used to administer particular examples of the multifunctional β-agonist compounds are those well-known in the art, such as, metered dose inhalers, liquid nebulizers, dry powder inhalers, sprayers, thermal vaporizers, and the like. Other suitable technology for administration of particular multifunctional β-agonist compounds includes electrohydrodynamic aerosolizers.

The abbreviations "MMAD" and "MMEAD" are well-known in the art, and stand for "mass median aerodynamic diameter" and "mass median equivalent aerodynamic diameter" respectively. The terms as used in the art are substantially equivalent. The "aerodynamic equivalent" size of a particle is the diameter of a unit density sphere which exhibits the same aerodynamic behavior as the particle, regardless of actual density or shape. MMAD is usually determined using a cascade impactor, which measures—the particle size as a function of the aerodynamic behavior of the particle in a high velocity airstream. The median (50%) particle size is obtained from a linear regression analysis of the cumulative distribution data. In one embodiment, the inhalation device delivers small particles, e.g., less than about 10 μm MMAD.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, N.C.), Diskus (Glaxo, Research Triangle Park, N.C.), the Ultravent nebulizer (Mallinckrodt), the Acorn II nebulizer (Marquest Medical Products, Totowa, N.J.) the Ventolin metered dose inhaler (Glaxo, Research Triangle Park, N.C.), or the like. In some examples, multifunctional β-agonist compounds can be delivered by a dry powder inhaler or a sprayer;

As those skilled in the art will recognize, the formulation of multifunctional β-agonist compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of multifunctional β-agonist compounds in the aerosol. For example, shorter periods of administration can be used at higher concentrations of multifunctional β-agonist compounds in the nebulizer solution. Devices such as metered dose inhalers can produce higher aerosol concentrations, and can be operated for shorter periods to deliver the desired amount of multifunctional β-agonist compounds in some embodiments. Devices such as dry powder inhalers deliver active agent until a given charge of agent is expelled from the device. In this type of inhaler, the amount of multifunctional β-agonist compounds in a given quantity of the powder determines the dose delivered in a single administration. The formulation of multifunctional β-agonist compound is selected to yield the desired particle size in the chosen inhalation device.

Dry powder generation typically employs a method such as a scraper blade or an air blast to generate particles from a solid formulation of multifunctional β-agonist compounds. The particles are generally generated in a container and then transported into the lung of a patient via a carrier air stream. Typically, in current dry powder inhalers, the force for breaking up the solid and air flow is provided solely by the patient's inhalation. One suitable dry powder inhaler is the Turbohaler manufactured by Astra (Wilmington, Del.).

Formulations of multifunctional β-agonist compounds for administration from a dry powder inhaler may typically include a finely divided dry powder containing multifunctional β-agonist compounds, but the powder can also include a bulking agent, buffer, carrier, excipient, another additive, or the like. Additives can be included in a dry powder formulation of multifunctional β-agonist compounds, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like.

In some embodiments, a spray including multifunctional β-agonist compounds can be produced by forcing a suspension or solution of a particular multifunctional β-agonist compound through a nozzle under pressure. The nozzle size and configuration, the applied pressure, and the liquid feed rate can be chosen to achieve the desired output and particle size. An electrospray can be produced by an electric field in connection with a capillary or nozzle feed. Formulations of multifunctional β-agonist compounds suitable for use with a sprayer can include multifunctional β-agonist compounds in an aqueous solution at a concentration of about 1 mg to about 20 mg of multifunctional β-agonist compound per mL of solution. The formulation can include agents such as an excipient, a buffer, an isotonicity agent, a preservative, a surfactant, and/or, zinc. Multifunctional β-agonist compounds can be administered by a nebulizer, such as jet nebulizer or an ultrasonic nebulizer. Typically, in a jet nebulizer, a compressed air source is used to create a high-velocity air jet through an orifice.

Formulations of multifunctional β-agonist compound suitable for use with a nebulizer, either jet or ultrasonic, typically include multifunctional β-agonist compound in an aqueous solution. The formulation can include agents such as an excipient, a buffer, an isotonicity agent, a preservative, a surfactant, and/or zinc. The formulation can also include an excipient or agent for stabilization of the multifunctional β-agonist compound, such as a buffer, a reducing agent, a bulk protein, or a carbohydrate. Bulk proteins, surfactants, carbohydrates and other additives are useful in formulating multifunctional β-agonist compounds and can be used as described above.

In a metered dose inhaler (MDI), a propellant, multifunction, β-agonist compound, and any excipients or other additives are contained in a canister as a mixture including a liquefied compressed gas.

The present invention also relates to a pharmaceutical composition including multifunctional β-agonist compounds suitable for administration by inhalation. According to the invention, multifunctional β-agonist compounds can be mused for manufacturing a composition or medicament, including medicaments suitable for administration by inhalation. The invention also relates to methods for manufacturing compositions including multifunctional β-agonist compounds in a form that is suitable for administration, including administration by inhalation. For example, a dry powder formulation can be manufactured in several ways, using conventional techniques, such as described in any of the publications mentioned above and incorporated expressly herein by reference, and, for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the multifunctional β-agonist compounds in a suitable solvent, such as water, at an appropriate pH, including buffers or other excipients.

As known by those of skill in the art, the preferred dosage of multifunctional β-agonist compounds will depend on the age, weight, general health and severity of the respiratory disorder of the individual being treated. Dosage may also need to be tailored to the sex of the individual and/or the lung capacity of the individual. Dosage may also be tailored to individuals suffering from more than one respiratory disorder or those individuals who have additional conditions which affect lung capacity and the ability to breathe normally, for example, emphysema, bronchitis, pneumonia, respiratory infections, etc. Dosage, and frequency of administration of the multifunctional β-agonist compound will also depend on whether the compounds are formulated for treatment of acute episodes of the respiratory disorder or for the prophylactic treatment of the disorder. A skilled practitioner will be able to determine the optimal dose for a particular individual. Various formulations of the compounds and compositions described herein may be administered according to the variables described above. In particular, formulations for prophylactic treatment of respiratory conditions may be administered, daily, twice daily, thrice daily or four times daily and/or upon the occurrence of symptoms associated with the underlying respiratory condition. Such symptoms include wheezing, coughing, shortness of breath, tightness or pressure in the chest and the like. It is contemplated that individuals who are using a prophylactic formulation may on occasion need to administer doses in response to acute episodes of symptoms. Administration includes any of the methods or routes as described herein.

The compounds as described herein may be administered to an individual in need thereof over a period of time consistent with treatment of the respiratory disorder from which the individual suffers. In the case of pneumonia or other periodic disorders, the treatment may be discontinued when the individual is no longer affected by the disorder or deemed to be no longer in need of the treatment by a skilled practitioner. Examples of such time periods include days, weeks or months. Where the respiratory condition is a congenital or chronic disorder such as asthma, emphysema, AHR, COPD and others, it is envisioned that the treatment with the compounds described herein will be administered for a period of weeks, months, years or decades. The methods as described herein also include the administration of combinations of the compounds as described herein, or combinations of the compounds described herein and other drugs used in the treatment of the respiratory disorders described herein or symptoms associated with these disorders.

Drug delivery devices, such as metered inhalation devices, may be used to deliver the compounds of the invention by inhalation as described above.

Also provided are kits for administration of the multifunctional β-agonist compound or composition comprising at least one multifunctional β-agonist compound, that may include a dosage amount of at least one multifunctional β-agonist compound or a composition comprising at least one multifunctional β-agonist compound as disclosed herein. Kits may further comprise suitable packaging and/or instructions for use of the compound. Kits may also comprise a means for the delivery of the at least one multifunctional β-agonist compound or compositions comprising at least one multifunctional β-agonist compound, such as an inhaler, spray dispenser (e.g. nasal spray) or pressure pack for capsules, tables, or other device as described herein.

In another aspect of the invention, kits for treating an individual who suffers from or is susceptible to respiratory disorders are provided, comprising a container comprising a dosage amount of an multifunctional β-agonist compound or composition as disclosed herein, and instructions for use.

Kits may also be provided that contain sufficient dosages of the multifunctional β-agonist compound or composition to provide effective treatment for an individual for an extended period, such as a week, 2 weeks, 3, weeks, 4 weeks, 6 weeks or 8 weeks or more.

The invention is further illustrated by the following non-limiting examples.

EXAMPLES

Example 1

Synthesis of 5-{2-[(1-Yloxyl-2,2,5,5-tetramethyl-pyrrolidin-3-ylmethyl)-amino]-1-S-nitroso-ethyl}-1,1,3,3-tetramethylisoindolin-2-yloxyl, hydrochloride, compound 1:

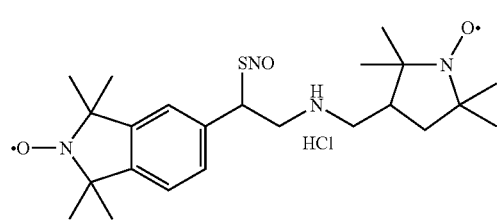

The compound in this example was synthesized as depicted in scheme 4 below:

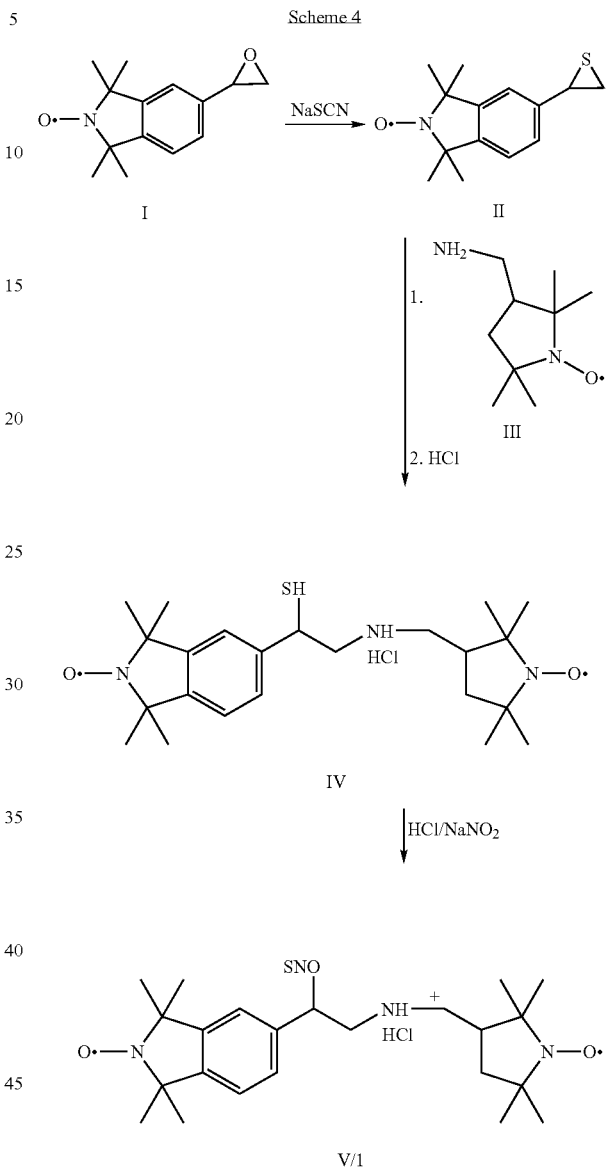

Synthesis of Epoxide 1:

The synthesis of epoxide 1 was performed as described in scheme 3.

2-Benzyl-1,1,3,3,-tetramethylisoindoline

To a solution of methyl Grignard reagent, prepared from methyl iodide (170 g, 1.2 mol) and magnesium turnings 930.4 g, 1.25 mol) in ether (700 ml) under nitrogen, was concentrated by slow distillation of solvent until the internal temperature reached 80° C. The residue was allowed to cool to 60° C., and a solution of N-benzylphthalimide (47.5 g, 0.2 mol) in toluene (600 ml) was added dropwise with stirring at a sufficient rate to maintain this temperature. When the addition was complete, solvent was distilled slowly from the mixture until the temperature reached 108-110° C. After being maintained at this temperature (reflux) for 4 hours, the mixture was concentrated to approximately 200 ml by further solvent distillation. It was then cooled and diluted with light petroleum (500 ml). The resulting slurry was filtered through Celite and washed with light petroleum (3×100 ml), the combined filtrate was kept in an open flask for approx. 2 h and then passed through a short column of basic alumina (activity 1). The column was further eluted with light petroleum until eluent was amine free. Evaporation of the pale yellow solution gave an oil which rapidly solidified (20 g 37%). Two crystallizations from methanol or ethanol gave colourless needles of 2-benzyl-1,1,3,3,-tetramethylisoindoline. m.p. 63-64° C. NMR (CDCl$_3$, 400 MHz) 1.3, s, 4 x CH$_3$; 4.05, s, ArCH2; 7.04-7.54, m, ArH.

1,1,3,3-Tetramethylisoindoline

A solution of 2-benzyl-1,1,3,3,-tetramethylisoindoline (5.5 g 20 mmol) in glacial acetic acid (20 ml) was hydrogenated at 60 lb/in$^2$ over 5% palladium/c for 3 h at room temperature. The suspension was filtered and the solvent removed at reduced pressure. The residue was dissolved in water and the solution was made alkaline (PH 9) by the addition of 10% sodium hydroxide and extracted with ether (3×50 ml). The combined organic extracts were dried and evaporated to dryness to give the title compound (3.5 g 96%), which was recrystallized from methanol/water. m.p. 36-38° C. NMR (CDCl$_3$, 400 MHz), 1.46 s, 4 x CH$_3$; 1.9 s, NH, D$_2$O exchanged; 7.1-7.27 m, ArH.

1,1,3,3-Tetramethylisoindoline-2-yloxyl

A solution of 1,1,3,3-tetramethylisoindoline (3.3 g 18.8 mmol) in methanol (35 ml) and acetonitrile (2.5 ml) was added sodium hydrogen carbonate (1.26 g, 15 mmol), sodium tungstate dihydrate (0.18 g, 0.55 mmol) and finally 30% aqueous hydrogen peroxide (7 ml, 62 mmol). The suspension was stirred at room temperature for 32 h to give a bright yellow solution, which was diluted with distilled water and extracted with light petroleum (3×75 ml). The combined organic layers were washed with 2N sulfuric acid and followed by brine. Drying and evaporation of the solvent gave 1,1,3,3-tetramethylisoindoline-2-yloxyl (3.1 g, 92%) as bright yellow solid, which was recrystalized from light petroleum. m.p. 128-129° C. m/e (70 eV) 190 (M, 38%).

1-(2-Yloxyl-1,1,3,3tetramethyl-isoindoline-5yl)-ethanone

AlCl$_3$ (1.6 g, 12 mmol) was added to a solution of 1,1,3,3-tetramethylisoindoline-2-yloxyl (1.9 g, 10 mmol) in chloroform (100 ml). To this suspension, acetyl chloride (0.86 g, 11 mmol) was added dropwise with stirring. When the addition was complete, the reaction mixture was refluxed for 2 h, cooled to room temperature and crushed ice was added. The organic phase was separated and washed twice with 1N NaOH (50 ml) and once with brine. The organic phase was dried and evaporated to dryness. The crude product was chromatographed on silica gel with hexane: ethylacetate (9:1) to give the pure product 1-(2-yloxyl-1,1, 3,3-tetramethyl-2,3-dihydro-1H-isoindol-5-yl)-ethanone (2.18 g, 95%). M$^+$ 232.

2-Bromo-1-(2-yloxyl-1,1,3,3-tetramethyl-isoindolin5-yl)-ethanone

To a solution of 0.1 mol of 1-(2-yloxyl-1,1,3,3-tetramethyl-isoindolin-5-yl)-ethanone and 0.1-0.2 g of dibenzoyl peroxide in 250 ml of CHCl$_3$ was added dropwise 1 equivalent of Br$_2$. The reaction mixture was stirred at room temperature until Br$_2$ color had disappeared, nitrogen was bubbled through the solution for 15-20 minutes, and the solvent was evaporated in vacuum. The residue was triturated with ether or recrystalized from the appropriate solvent to yield the corresponding bromoketone.

5-(2-Bromo-1-hydroxy-ethyl)-1,1,3,3-tetramethyl-isoindolin-2-yloxyl

Reduction of 2-bromo-1-(2-yloxyl-1,1,3,3-tetramethyl-isoindolin-5-yloxyl)-ethanone was achieved with borane and borane/oxazaborolidine (R or S) in THF to yield nonchiral and chiral bromohydrin, respectively. The product was obtained in 90-95% yield after purification by column chromatography (ethylacetate:hexane 1:4).

1,1,3,3-Tetramethyl-5-oxiranyl-isoindoline-2-yloxyl (I)

Treatment of 5-(2-Bromo-1-hydroxy-ethyl)-1,1,3,3-tetramethyl-isoindolin-2-yloxyl with suspension of NaH in THF generated the title epoxide in 85% yield.

1,1,3,3-Tetramethyl-5-thiiranyl-1,3-dihydro-isoindol-2-ol (II)

Epoxide (I) (10 mmol) was added to a solution of sodiumthiocyanate (12 mmol) in water (10 ml) and ethanol (7.5 ml), the solution was vigorously stirred at room temperature for 36 h. After cooling, the precipitated sodium cyanate was filtered off and the filtrate was extracted with ether, washed twice with brine, dried with sodium sulfate and evaporated to dryness. The residue was chromatographed on silica gel (ethylacetate:hexane, 1:9).

Synthesis of the amine III, 3-Aminomethyl-2,2,5,5-tetramethyl-pyrrolidin-2-yloxyl This compound was synthesized according to the scheme 5 below:

Scheme 5

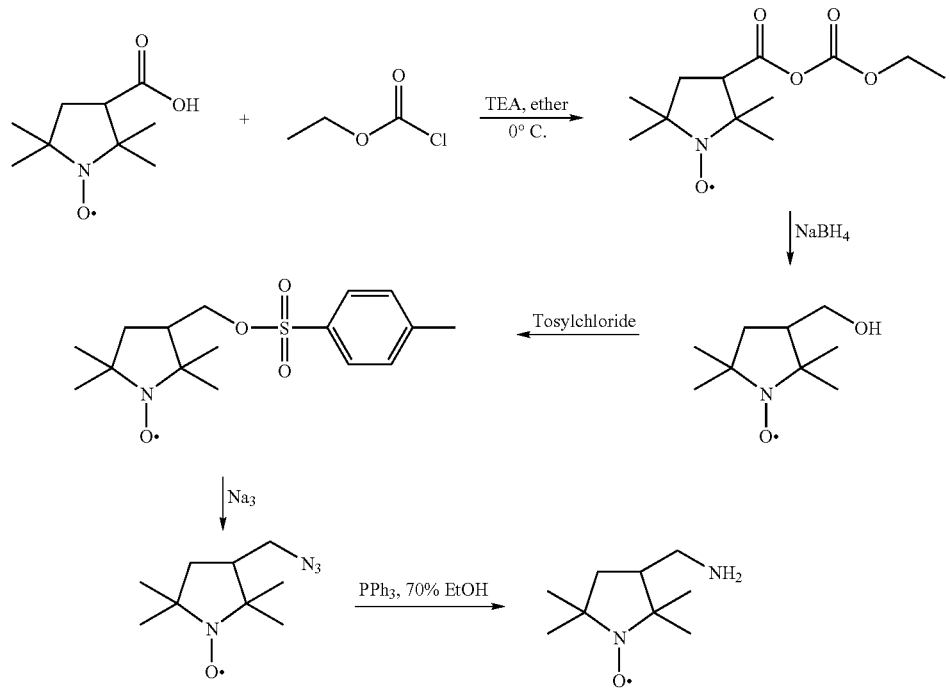

3-Hydroxymethyl-2,2,5,5-tetramethyl-pyrrolidin-1-yloxyl

To an ice cooled suspension of 2,2,5,5-tetramethyl pyrrolidine carboxylic acid (18.4 g, 0.1 mol) in dry ether (250 ml) and triethylamine (14 ml, 0.1 mol), ethylchloroformate (10.08 g, 0.1 mol) was added with vigorous stirring. The reaction mixture was stirred at 0° C. for 2 h. Ice cold water (100 ml) was then added and the organic phase was washed with 100 ml of ice cold 1N HCL (100 ml), water (100 ml), 5% $Na_2CO_3$ solution (100 ml) and water. The organic phase was dried and evaporated to dryness to give (18 g, 70%) of the mixed anhydride as a red oily product, which was reduced in an ethanolic suspension of $NaBH_4$ (3.12 g, 1.2 eq) at room temperature for 1 h. Ethanol was evaporated and the residue was partitioned between water and ether. The organic phase is separated and washed with distilled water and brine, dried and evaporated to dryness to give 3-Hydroxymethyl-2,2,5,5-tetramethyl-pyrrolidin-1-yloxyl (9.7 g, 56%), which can be recrystalized with ether-hexane.

3-Tosyl-2,2,5,5-tetramethyl-pyrrolidin-1-yloxyl

To a stirred pyridine solution of 3-Hydroxymethyl-2,2,5,5-tetramethyl-pyrrolidin-1-yloxyl (1.7 g, 10 mmol), that was cooled to 0° C., para-toluenesulfonyl chloride (1.9 g, 10 mmol) was added in three portions and the reaction mixture is stirred for further 3 h at room temperature. Pyridine was evaporated and the residue was dissolved in chloroform, washed twice with 1N HCl, 5% sodium carbonate solution and water. The organic phase was dried with sodium sulfate and evaporated to dryness to give a yellow crystals of 3-Tosyl-2,2,5,5-tetramethyl-pyrrolidin-1-yloxyl (3 g, 91%) which can be recrystalized from chloroform/hexane.

3-Azidomethyl-2,2,5,5-tetramethyl-pyrrolidin-1-yloxyl

Sodium azide (0.975 g, 15 mmol) and 3-Tosyl-2,2,5,5-tetramethyl-pyrrolidin-1-yloxyl (3.27 g, 10 mmol) in acetonitrile (100 ml), were reflux for three hours, and cooled to room temperature. The reaction was filtered and the acetonitrile was evaporated to dryness. The residue was dissolved in chloroform and washed twice with distilled water, dried and evaporated to dryness to afford the title compound (1.8 g, 91%) that can be recrystalized from chloroform hexane.

3-Aminomethyl-2,2,5,5-tetramethyl-pyrrolidin-1-yloxyl

To 3-Azidomethyl-2,2,5,5-tetramethyl-pyrrolidin-1-yloxyl (1.97 g, (10 mmol) in 70% ethanol, triphenyl phosphine (1.5 eq) was added and the solution was stirred at room temperature for 4 h. after the reaction was completed, it was extracted with ether and the ether fraction was washed twice with distilled water and brine. The ether was dried with sodium sulfate and evaporated to dryness to give a red solid residue which was crystallized from chloroform hexane (1.5 g, 87%).

5-{2-[(1-Yloxyl-2,2,5,5-tetramethyl-pyrrolidin-3-ylmethyl)-amino]-1-nitroso-ethyl}-1,3,3-tetramethylisoindolin-2-yloxyl, hydrochloride (compound 1)

A mixture of compound III (10 mmol) and 1 ml of N,O-bis-(trimethylsilyl)-acetamide in 50 ml of DMSO was stirred under nitrogen for 30 minutes at room temperature. A solution of compound II in 50 ml of DMSO was added and the solution was heated at 80° C. for 48 h. the mixture was cooled and the solvent was vacuum distilled (0.1 mm). The residue was purified by column chromatography on neutral alumina eluting with ethylacetate:hexane (1:3). This compound IV is dissolved in 10 ml of 8N HCl, stirred and cooled in an ice bath. Three mol equivalents of sodium nitrite is dissolved in distilled water and added dropwise to the reaction mixture. After 20 minutes, when most of the sodium nitrite was added, the title S-nitroso compound V/compound 1 separated as pale orange powder. Stirring is continued for 30 minutes in the cold bath and the precipitated product is filtered, washed twice with cold diluted HCl, dried in the desecrator and stored in airtight containers under nitrogen at −20° C. until use. MS and spectroscopic data of this compound V/compound 1 were found as expected for S-nitroso thiols.

Example 2

Synthesis of 5-(2-tert-Butylamino-1-S-nitroso-ethyl)-1,1,3,3-tetramethyl-isoindolin-2-yloxyl, compound 2:

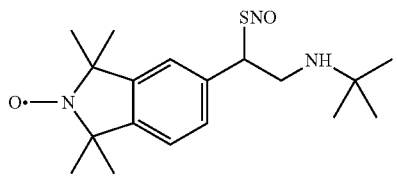

This compound was prepared as described in the following scheme:

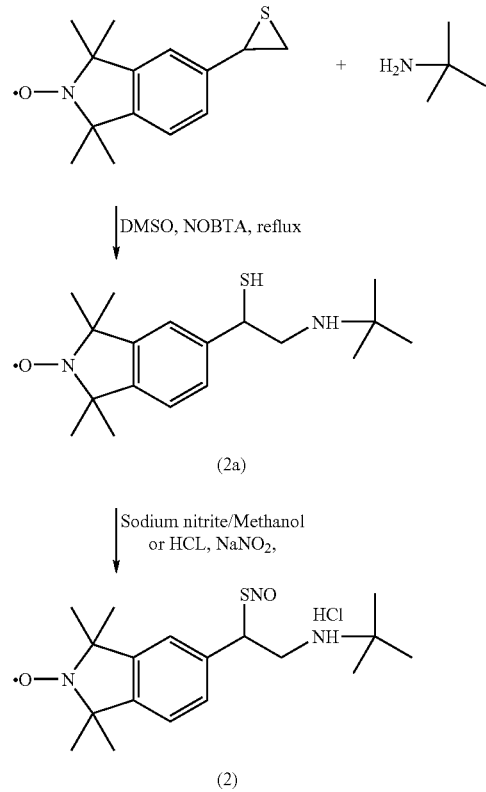

A mixture of tert-butylamine (10 mmol) and 1 ml of N,O-bis-(trimethylsilyl)-acetamide in 50 ml of DMSO was stirred under nitrogen for 30 minutes at room temperature. A solution of the thiirane (compound II) in 50 ml of DMSO was added and the solution was heated at 80° C. for 48 h. the mixture was cooled and the solvent was vacuum distilled (0.1 mm). The thiol-containing residue 2a was purified by column chromatography on neutral alumina eluting with ethylacetate:hexane (1:4). This compound 2a is dissolved in 10 ml of 8N HCl, stirred and cooled in an ice bath. Three mol equivalents of sodium nitrite is dissolved in distilled water and added dropwise to the reaction mixture. After 20 minutes, when most of the sodium nitrite was added, the title S-nitroso compound 2 separated as a pale orange powder. Stirring is continued for 30 minutes in the cold bath and the precipitated product is filtered, washed twice with cold diluted HCl, dried in the dessicator and stored in airtight containers under nitrogen at −20° C. until use. MS and spectroscopic data of this compound 2 were found as expected for S-nitroso thiols.

Example 3

Synthesis of 5-[1-Hydroxy-2-(2-S-nitroso-1-methyl-2,2-diphenyl-ethylamino)ethyl]-1,1,3,3-tetramethyl-isoindoline-2-Yloxyl, compound 3:

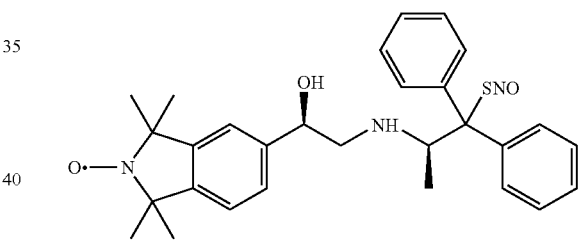

This compound was synthesized as illustrated in the following scheme:

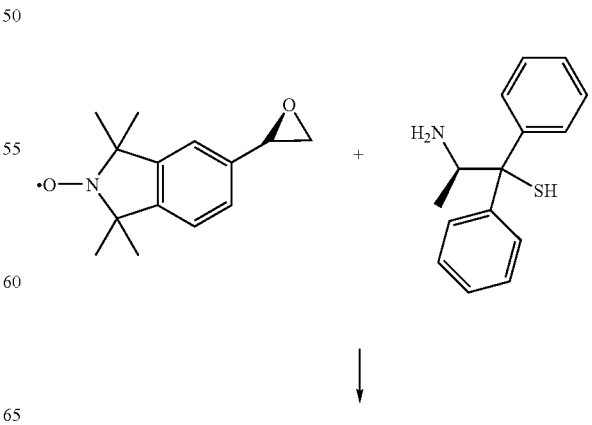

-continued

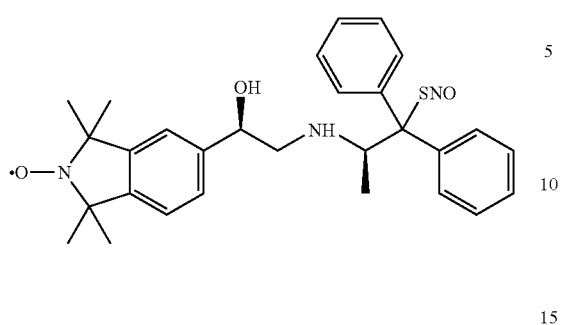

The amine utilized for this synthesis was synthesized as described in the following scheme:

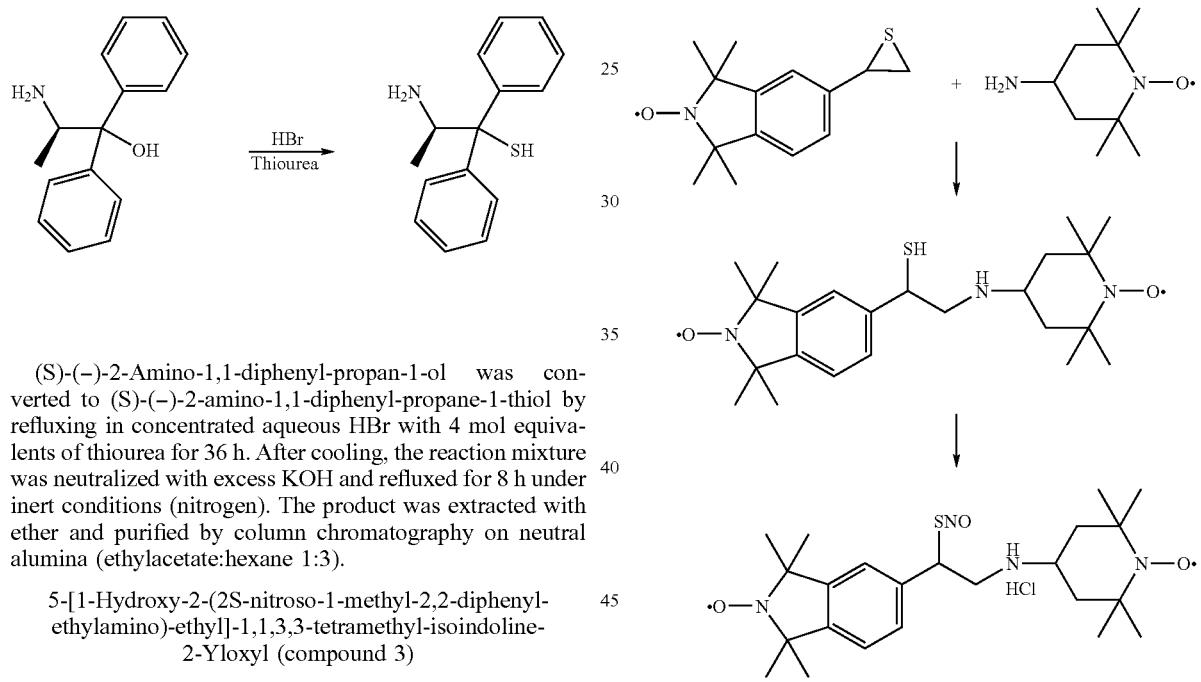

(S)-(−)-2-Amino-1,1-diphenyl-propan-1-ol was converted to (S)-(−)-2-amino-1,1-diphenyl-propane-1-thiol by refluxing in concentrated aqueous HBr with 4 mol equivalents of thiourea for 36 h. After cooling, the reaction mixture was neutralized with excess KOH and refluxed for 8 h under inert conditions (nitrogen). The product was extracted with ether and purified by column chromatography on neutral alumina (ethylacetate:hexane 1:3).

5-[1-Hydroxy-2-(2S-nitroso-1-methyl-2,2-diphenyl-ethylamino)-ethyl]-1,1,3,3-tetramethyl-isoindoline-2-Yloxyl (compound 3)

A mixture of the amine thiol (10 mmol) and 1 ml of N,O-bis-(trimethylsilyl)-acetamide in 50 ml of DMSO was stirred under nitrogen for 30 minutes at room temperature. A solution of the epoxide (compound I) in 50 ml of DMSO was added and the solution was heated at 80° C. for 48 h. the mixture was cooled and the solvent was vacuum distilled (0.1 mm). The residue was purified by column chromatography on neutral alumina with ethylacetate:hexane (1:3). This compound is dissolved in 10 ml of 8N HCl, stirred and cooled on an ice bath. Three mol equivalents of sodium nitrite is dissolved in distilled water and added dropwise to the reaction mixture. After 20 minutes, when most of the sodium nitrite was added, the title S-nitroso compound 3 separated as pale orange powder. Stirring is continued for additional 30 minutes in the cold and the precipitated product is filtered, washed twice with cold diluted HCl, dried in the dessicator and stored in airtight containers under nitrogen at −20° C. until use. MS and spectroscopic data of this compound were found as expected for S-nitrosothiols.

Example 4

Synthesis of 5-[2-(4-amino-2,2,6,6-tetramethyl-piperidin-1-yloxyl)-1-S-nitrosothiol-ethyl]-1,1,3,3-tetramethylisoindolin-2-yloxyl (compound 4).

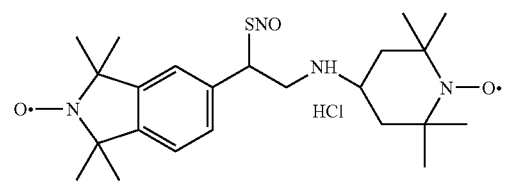

This compound was synthesized as shown in the following scheme:

The amine (4amino-TEMPO) was synthesized according to the following scheme (NaTg is Na$_2$WO$_4$):

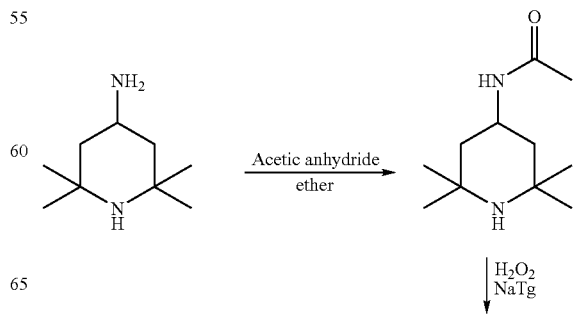

-continued

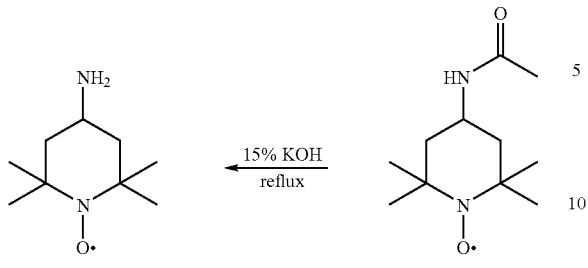

4-Acetylamino-2,2,6,6-Tetramethyl-piperidin

Acetic anhydride (70 g, 0.686 mol) was added dropwis to an ice cooled solution of 4-Amino-2,2,6,6-Tetramethyl-piperidin (34.6 g. 0.221 mol) in ether (100 ml). After the addition was complete (about 1 h), the reaction mixture was stirred for 30 minutes at room temperature. The precipitated white product, 4-acetylamino-2,2,6,6-Tetramethyl-piperidin (55.6 g, 98%) was filtered off and washed with ether and air dried. m.p. 175° C. subl.

4-Acetylamino-2,2,6,6-tetramethyl-piperidin-1-yloxyl 55.6 g of 4-acetylamino-2,2,6,6-Tetramethyl-piperidin was dissolved in 400 ml of water and basified with 50 g of potassium carbonate. To this solution was added 80 ml of 30% hydrogen peroxide, 4 g of sodium tungstenate (NaTg) and 4 g of EDTA, The mixture was stirred at room temperature for 72 h and the red precipitate filtered off and washed with distilled water to give the title compound (36.8 g). The filtrate was further extracted with dichloromethane to give more 7.1 of the product (overall yield 97%). m.p. 145-147° C.

4-Amino-2,2,6,6-tetramethyl-piperidin-1-yloxyl 11 g of 4-acetylamino-2,2,6,6-Tetramethyl-piperidin-1-yloxyl was hydrolyzed by refluxing in 25 ml of 15% KOH for 12 h. The reaction mixture was saturated with potassium carbonate and extracted with ether (2×50 ml). The ether was dried with sodium sulfate and the crude product was vacuum distilled (97-98/4 mm Hg) to give the pure 4-amino-2,2,6, 6-Tetramethyl-piperidin-1-yloxyl (8 g, 73%) as a deep red crystals. m.p. 34-35° C.

5-[2-(4-amino-2,2,6,6-tetramethyl-piperidin-1-yloxyl)-1-nitrosothiol-ethyl]-1,1,3,3-tetramethyl-isoindolin-2-yloxyl (compound 4)

A mixture of 4-amino-TEMPO (10 mmol) and 1 ml of N,O-bis-(trimethylsilyl)-acetamide in 50 ml of DMSO was stirred under nitrogen for 30 minutes at room temperature. A solution of the thiirane (compound II) in 50 ml of DMSO was added and the solution was heated at 80° C. for 48 h. the mixture was cooled and the solvent was vacuum distilled (0.1 mm). The residue was purified by column chromatography on neutral alumina eluting with ethylacetate:hexane (1:3). This compound is dissolved in 10 ml of 8N HCl, stirred and cooled in an ice bath. Three mol equivalents of sodium nitrite is dissolved in distilled water and added dropwise to the reaction mixture. After 20 minutes, when most of the sodium nitrite was added, the title S-nitroso compound 4 separated as an orange powder. Stirring is continued for 30 minutes in the cold bath and the precipitated product is filtered, washed twice with cold diluted HCl, dried in the dessicator and stored in airtight containers under nitrogen at −20° C. until use. MS and spectroscopic data of this compound were found as expected for S-nitroso thiols.

Example 5

Synthesis of 5-[1-Hydroxy-2-(2-S-nitroso-1,2-diphenyl-ethylamino)-ethyl]-1,1,3,3-tetramethyl-1,3-dihydroisoindolin-2-yloxyl (compound 5)

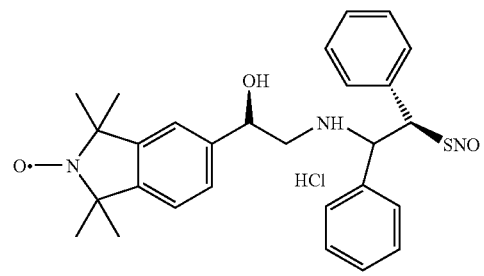

This compound was synthesize as described in the following scheme:

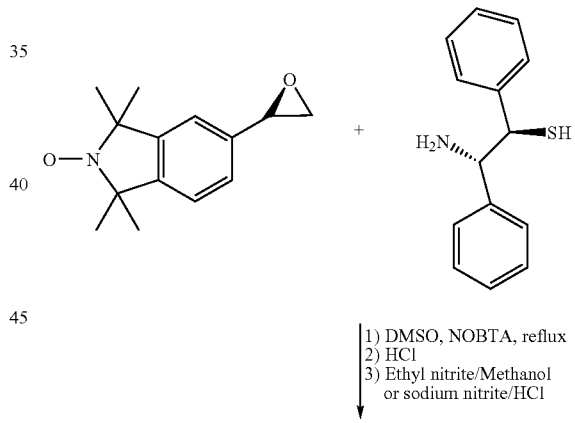

1) DMSO, NOBTA, reflux
2) HCl
3) Ethyl nitrite/Methanol or sodium nitrite/HCl

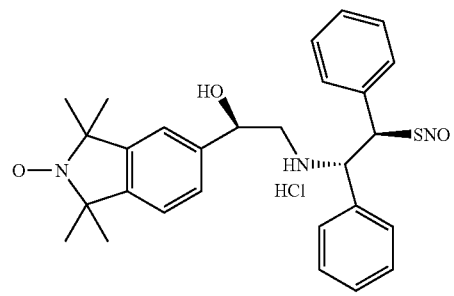

The amine utilized for this synthesis was synthesized as described in the following scheme:

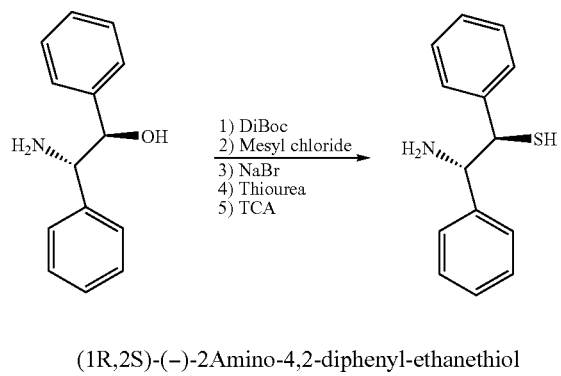

(1R,2S)-(−)-2Amino-4,2-diphenyl-ethanethiol

The starting (1R,2S)-(−)-2-amino-1,2-diphenylethanol was first protected with the Boc group using di-tert-butyl-dicarbonate in dioxane, followed by mesylating the hydroxyl group with methanesulfonyl chloride in dichloromethane/triethylamine solution. The mesylate was treated with NaBr in acetone to yield the bromide, which is then treated with thiourea to produce the mercapto compound with the protected amine. This later compound was finally treated with trichloroacetic acid to liberate the amino group and give the title compound.

5-[1-Hydroxy-2-(2-S-nitroso-1,2-diphenyl-ethylamino)-ethyl]-1,1,3,3-tetramethyl-1,3-dihydro-isoindolin-2-yloxyl (compound 5)

A mixture of the amine (10 mmol) and 1 ml of N,O-bis-(trimethylsilyl)-acetamide in 50 ml of DMSO was stirred under nitrogen for 30 minutes at room temperature. A solution of the epoxide (compound I) in 50 ml of DMSO was added and the solution heated at 80° C. for 48 h. After cooling, the solvent was vacuum distilled (0.1 mm), and the residue purified by column chromatography on neutral alumina with ethylacetate:hexane (1:3). This compound is dissolved in 10 ml of 8N HCl, stirred and cooled in an ice bath. Three mol equivalents of sodium nitrite is dissolved in distilled water and added dropwise to the reaction mixture. After 20 minutes, when most of the sodium nitrite was added, the title S-nitroso compound 5 separated as pale orange powder. Stirring is continued for 30 minutes in the cold bath and the precipitated product is filtered, washed twice with cold diluted HCl, dried in the dessicator and stored in airtight containers under nitrogen at −20° C. until use. MS and spectroscopic data of this compound were found as expected for S-nitrosothiols.

Example 6

Synthesis of N-(5-{2-[(4,4-Dimethyl-[1,2]dithiolan-3-ylmethyl)-amino]-1-nitroxy-ethyl}-2-hydroxy-phenyl)-formamide, hydrochloride, compound 6.

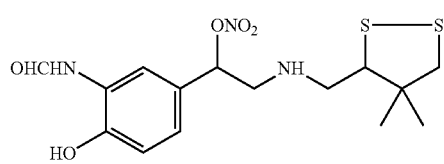

This compound was prepared as illustrated in the following scheme:

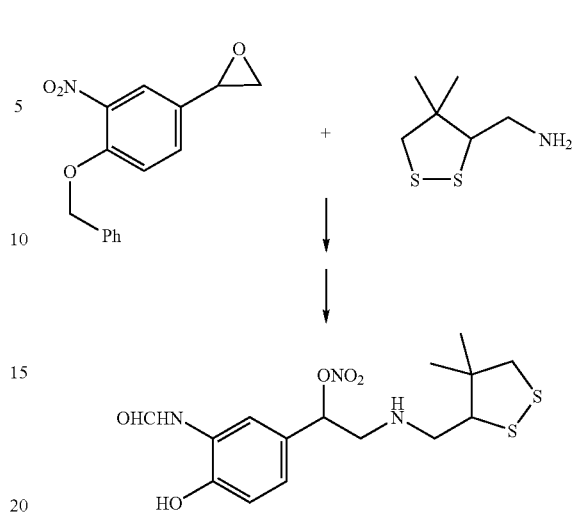

The amine used for the synthesis of this compound was synthesized as described in the following scheme:

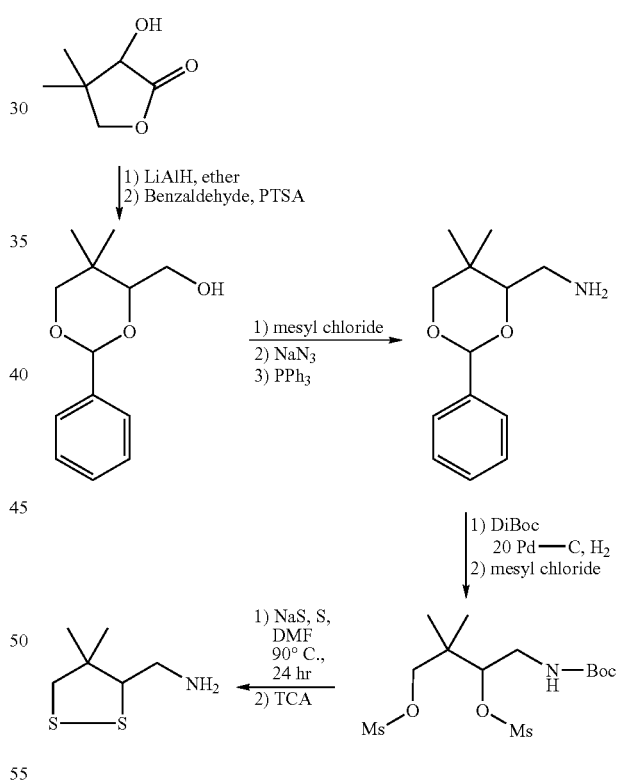

(+)-4,4-Dimethyl-[1,2]dithiolan-3-yl)-methylamine (+)-Pantholactone (or DL) was reduced with LiAlH in ether to give 3,3-dimethyl-butane-1,2,4-triol in 60% yield, which was protected as a 6 membered acetonide by treatment with benzaldehyde in benzene under triflouroacetic acid catalysis in 90% yield. The remaining free hydroxyl group was converted to the amine by the same method used for the preparation of the amine in example 6, which was further protected with the Boc group. Deprotection of the hydroxyl groups by catalytic hydrogenation followed by dimesylation of the obtained 2,4-diol gave the dimesylate, which was converted to the disulfide using sulfur and sodium sulfide in DMF under standard dithiolation conditions. Finally, the amine was deprotected with trichloroacetic acid in dichloromethane to afford the title amino compound 6.

The amine was treated with the corresponding epoxide, followed by generation of the hydrochloride salt and nitration in the same manner as described for example 7 to yield the hydrochloride salt of the title compound N-(5-{2-[(4,4-dimethyl-[1,2]dithiolan-3-ylmethyl)-amino]-1-nitrooxy-ethyl}-2-hydroxy-phenyl)-formamide.

Example 7

Synthesis of [2-(2,2-Dimethyl-4H-benzo[1,3]dioxin-6-yl)-2-nitrooxy-ethyl]-(5-[1,2]dithiolan-3-yl-pentyl)-amine hydrochloride, 7:

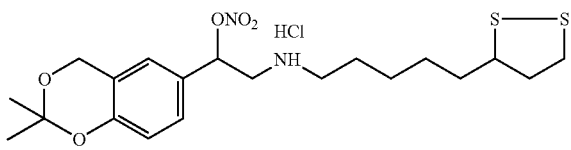

This compound was synthesized as illustrated in the following scheme:

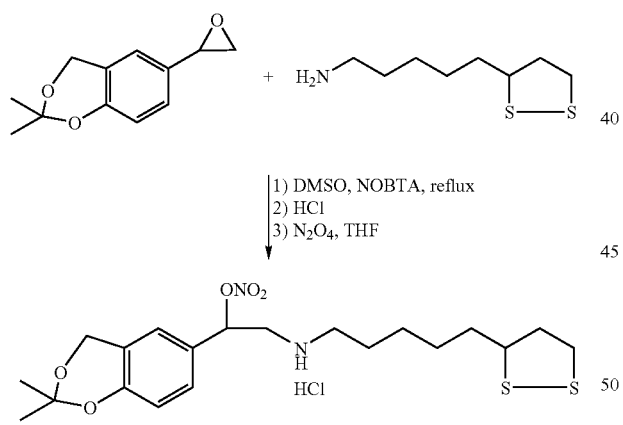

The starting materials for the synthesis of this compound were synthesized as following:

I—2,2-Dimethyl-6-oxiranyl-4H-benzo[1,3]dioxine

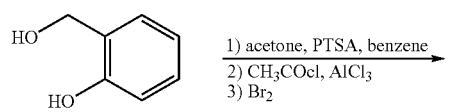

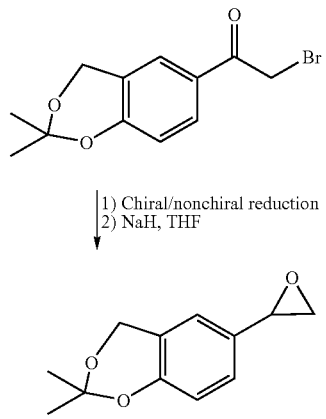

First the hydroxyl groups of Salicyl alcohol were protected with acetone in refluxing benzene with the catalysis of para-toluenesulfonic acid to give 2,2-Dimethyl-4H-benzo[1,3]dioxine in quantitive yield. Friedel-craft acylation of this compound with AlCl₃ and acetyl chloride in refluxing chloroform afforded 1-(2,2-dimethyl-4H-benzo[1,3]dioxin-6-yl)-ethanone in good yield. This was further brominated in chloroform with the catalysis of benzoyl peroxide to give 2-bromo-1-(2,2-dimethyl-4H-benzo[1,3]dioxin-6-yl)-ethanone, which was reduced to the chiral or nonchiral bromohydrine with borane and borane/oxazaborolidine, respectively. The title epoxide was generated by the addition of the above bromohydrine to a suspension of NaH in THF, as described previously.

II—5-[1,2]Dithiolan-3-yl-pentylamine (lipoyl amine)

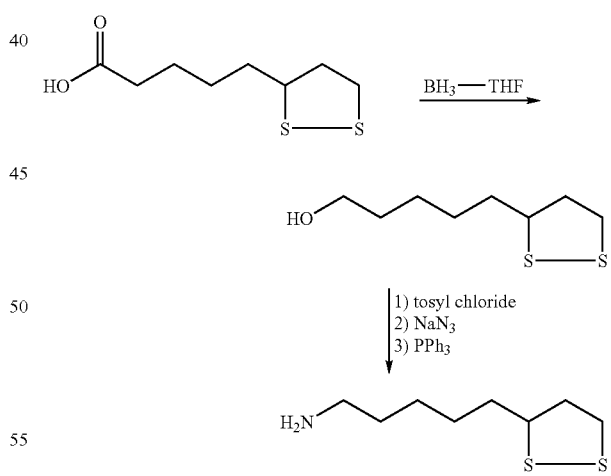

Lipoyl alcohol was obtained as a yellow oil in 95% yield by the reduction of lipoic acid with borane-THF complex in dry THF, and purification by column chromatography. The alcohol was converted to the tosylate with paratoluenesulfonyl chloride under standard conditions. The azide compound was generated by the reaction of the tosylate with NaN₃ in acetonitrile. Finally, the lipoyl amine was obtained by reaction of the lipoyl azide with triphenylphosphine in 70% aqueous ethanol. The overall yield of lipoyl amine (from lipoic acid) is in the range of 75-80%.

[2-(2,2-Dimethyl-4H-benzo[1,3]dioxin-6-yl)-2-nitroxy-ethyl]-(5-[1,2]dithiolan-3-yl-pentyl)-amine (compound 7)

A mixture of lipoyl amine (10 mmol) and 1 ml of N,O-bis-(trimethylsilyl)-acetamide in 50 ml of DMSO was stirred under nitrogen for 30 minutes at room temperature. A solution of the epoxide in 50 ml of DMSO was added and the solution was heated at 80° C. for 48 h. After cooling, the solvent was vacuum distilled (0.1 mm) and the residue was purified by column chromatography on neutral alumina with ethylacetate:hexane (1:4). This compound is converted to the hydrochloride salt by bubbling of gaseous HCl to its methanolic solution and precipitating with ether. The title nitro compound 7 was obtained by bubbling nitrogen dioxide gas in THF solution of the hydrochloride salt with stirring. The product was stored in airtight containers under nitrogen at −20° C. until use.

Example 8

Synthesis of N-{5-[2-(5-[1,2]Dithiolan-3-yl-pentylamino)-1-nitrooxy-ethyl]-2-hydroxy-phenyl}-formamide hydrochloride, compound 8:

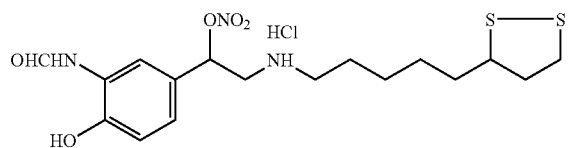

This compound was synthesized according to the following scheme:

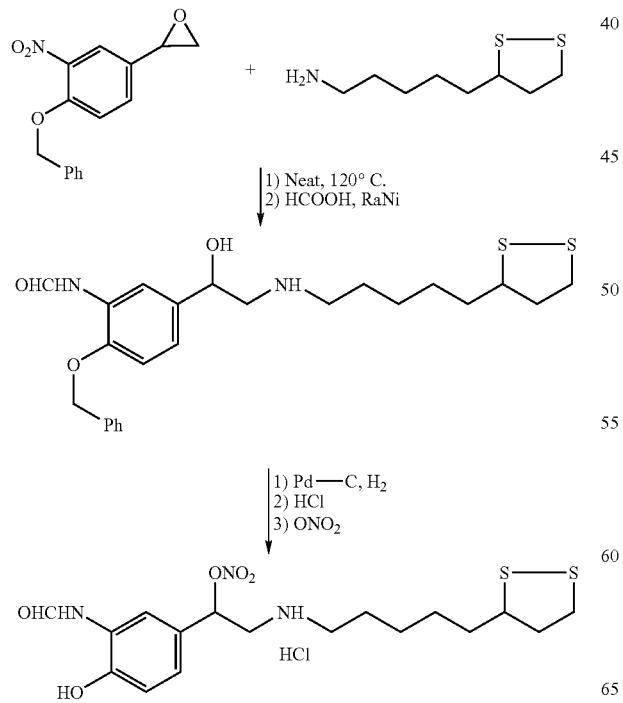

The epoxide (2-(4Benzyloxy-3-nitro-phenyl)oxirane) utilized for the synthesis of this compound was synthesized as described in the following scheme:

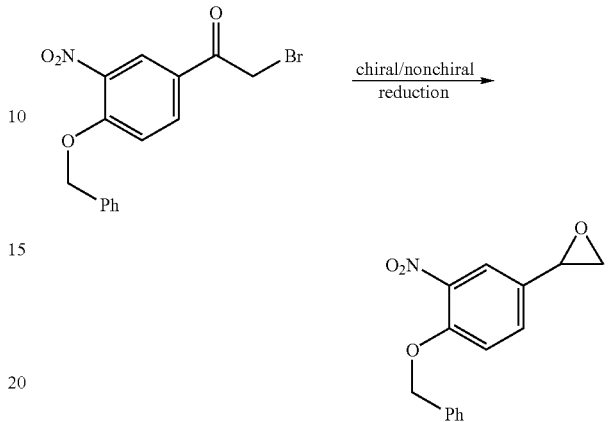

A mixture of lipoyl amine and the epoxide were heated at 120° C. until all epoxide has disappeared (monitored by TLC), followed by selective reduction of the nitro group in formic acid afforded the formamide that was purified by chromatography and hydrogenated to deprotect the hydroxyl group. This compound was converted to the hydrochloride salt by treatment with gaseous HCl in methanol and precipitated with ether. Treatment of the obtained salt in THF with nitrogen dioxide afforded the title compound 8.

Example 9

Synthesis of 5-[1-Hydroxy-2-(4-S-nitroso-4-methyl-cyclohexylamino)-1,1,3,3-tetramethyl-1,3-dihydro-isoindol-2-yloxy, free radical, compound 9:

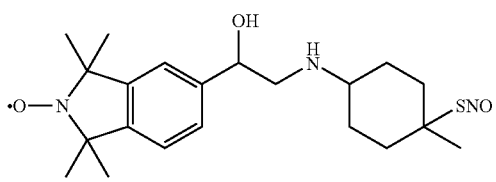

This compound was synthesized by reacting epoxide I in Example 1 with the corresponding amine followed by hydrochloride salt formation and S-nitrosylation by either sodium nitrite or ethyl nitrite. The amine(4-mercapto4-methyl cyclohexylamine) was synthesized from the commercially available 4-hydroxy cyclohexylamine by standard methods involving amine protection (Boc), oxidation, thiolation and reacting with methyl magnesium iodide. The resulting N-protected 4-mercapto-4-methyl cyclohexylamine was deprotected and reacted with epoxide I as described above.

Example 10

Synthesis of 5-{1-Hydroxy-2-[1-S-nitroso-1-methyl-ethyl)-cyclohexylamino]-ethyl}-1,1,3,3-tetramethyl-1,3-dihydro-isoindol-2yloxy, free radical, compound 10:

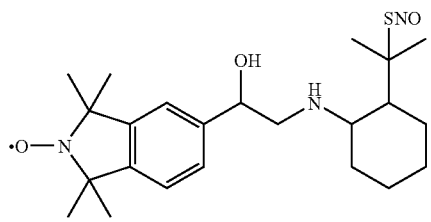

This compound was synthesized by reacting epoxide I in Example 1with the corresponding amine followed by hydrochloride salt formation and S-nitrosylation by either sodium nitrite or ethyl nitrite, as described above. The amine (8-mercapto menthylamine) was synthesized from the commercially available 8-mercapto menthone by standard methods involving S-protection and reductive amination. The resulting S-protected menthylamine was deprotected and reacted with epoxide I as described above.

Example 11

Biological Activity

The potency and efficacy of the multifunctional β-agonist compounds are evaluated using a model of biological response for asthma as described below, where increased relaxation is an in vitro indication of increased efficacy, and is a predictive model for in vivo efficacy. The assays as described here are also described in, for example, U.S. Pat. No. 4,992,474 and Jansen et al.(1992) *J. Pharmacol. Exptl. TherapeuticsI* 261(1):154-160.

Tissue Preparation

Male Hartley guinea pigs (500-600 g) were anesthetized by intraperitoneal injection of ketamine and xylazine (50 and 10 mg/kg, respectively). The heart and lungs were excised en bloc and tracheas were removed and placed in Krebs-Henseleit buffer composed of (mM): NaCl 118, KCl 5.4, $NaH_2PO_4$ 1.01, $NaHCO_3$ 25, $MgSO_4$ 0.69, $CaCl_2$ 2 2.32, glucose 11.1, pH 7.4. Tracheas were then dissected free from surrounding fat and connective tissue and cut into 1-2-mm thick rings. The tracheal rings were then placed in buffer and continuously gassed with 95% $O_2$ and 5% $CO_2$.

Relaxation Studies

Tracheal rings were suspended on stainless steel hooks in 10 ml of oxygenated (95% $O_2$, 5% $CO_2$) Krebs-Henseleit buffer at 37° C. and connected to transducer (Experimetria Model) for recording changes in isometric force. The tracheal rings were equilibrated for 60 min under a load of 1 g and then primed twice by exposure to 100 µM methacholine. Tissues were contacted with methacholine, histamine, or leukotriene $D_4$ at concentrations determined to approximately generate 50% of maximal tone, after which cumulative relaxation-response curves were constructed. To construct these curves, the initial contraction was assigned a value of 100% and the bath concentration of the tested compound required to achieve 50% relaxation (i.e., $IC_{50}$) determined by linear interpolation.

FIG. 1 shows the results with salbutamol (open squares); compound 2 (filled circles); and its non-nitrosylated precursor, compound 2a (open triangles). As shown in FIG. 1, compound 2 is a more effective relaxant compound than either salbutamol or the non-nitrosolated precursor of compound 2, compound 2a, which incorporates the ROS scavenger and β-agonist moiety of salbutamol, but not the NO donor moiety. Thus, compound 2 is much more effective at a lower concentration than either compound 2a or salbutamol.

Cyclic Nucleotide Assays

Tracheal rings in Krebs-Heneseleit solution were exposed to a 5-100 µM of the test compound for 30-90 seconds. Reaction was terminated by the addition of ice-cold 10% trichloroacetic acid and rapidly frozen in ethanol-saturated dry ice. In the methylene blue experiment, rings were pre-exposed methylene blue, a guanylyl cyclase inhibitor, for 30 min. Tissues were then individually pulverized with a glass homogenizer and centrifuged at 8000×g for 5 min. The clear supernatant was extracted with water-saturated ether and assayed for cGMP using commercially available radioimmunoassay kits as described by the manufacturer (Amersham Biosciences, Piscataway, N.J.).

As indicated by FIG. 2, compound 2 elevates the production of cGMP, indicative of NO-guanylyl cyclase pathway activity. Compound 2a, the non-nitrosolated precursor of compound 2, does not stimulate the production of cGMP compared to the control compound or salbutamol. Incubation with methylene blue, a guanylyl cyclase inhibitor, reduces the efficacy of compound 2, as would be expected for a mechanism of action which includes NO-guanylyl cyclase pathway activity. From these results it can be seen that the added activity of compound 2 compared to compound 2a is due to the NO-donating properties of compound 2.

All publications, patents, and patent applications referred to herein are hereby incorporated herein by reference in their entirety.

What is claimed is:

1. A multifunctional β-agonist compound having reactive oxygen species (ROS) scavenger groups and nitric oxide (NO) donor groups being ROS scavenger and NO donor of Formula 1:

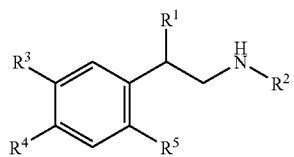

or its salt or a solvate thereof or an optical isomer thereof, wherein $R^1$ is —SNO;

$R^2$ is ROS scavenger group or a NO donor group connected to the —NH group via a linker made of $C_5$-$C_8$ cyclic alkyl, or straight or branched $C_1$-$C_{15}$ alkyl in which one carbon atom is optionally replaced by oxygen or nitrogen, wherein said ROS scavenger group is selected from a nitroxide free radical, alkenyl, sulfhydryl or dithiol moiety in oxidized or reduced form, and aryl, and wherein said NO donor group is selected from —ONO, —$ONO_2$, —SNO, and —NONOate or $R^2$ is $C_5$-$C_8$ cyclic alkyl, or straight or branched $C_1$-$C_{15}$ alkyl;

$R^3$ and $R^4$ together form a substituted 5 to 7-membered saturated heterocycle having 1 or 2 heteroatoms independently selected from nitrogen, oxygen, and sulfur, wherein one of said nitrogen atoms being optionally substituted by oxygen to form a nitroxide radical;

$R^5$ is selected from the group consisting of —H and straight or branched chain $C_1$-$C_{15}$ alkyl;

and whereas any of said alkyl groups is optionally substituted with one or more functional groups selected from hydroxyl, bromo, fluoro, chloro, iodo, mercapto thio, cyano, alkylthio, aryl, carboxyl, carbalkoyl, alkenyl, nitro, amino, alkoxyl, or amido;

wherein $R^2$ is said ROS scavenger if said saturated heterocycle does not have the nitrogen atom substituted by oxygen.

2. A β-agonist compound according to claim 1, wherein said saturated heterocycle is selected from the group consisting of pyrrolidine, oxazolidine, thiazolidine, tetrahydro 1,3-oxazine, 1,3-dioxane, piperidine, 3-thiapiperidine, and 1,3-thiazine.

3. A β-agonist compound according to claim 1, wherein the nitroxide free radical is a heterocyclyl moiety having the nitrogen atom within a 5-, 6- or 7-membered ring which optionally contains another heteroatom selected from oxygen and sulfur at position beta to the nitrogen, and which is substituted with methyl or ethyl at positions alpha to the nitrogen.

4. The β-agonist compound of claim 3, wherein said heterocyclyl moiety is linked to the β-agonist moiety via sharing of 1 to 2 atoms, or via a linker.

5. A n-agonist compound according to claim 1, wherein said ROS scavenger group is selected from the group consisting of the following moieties:

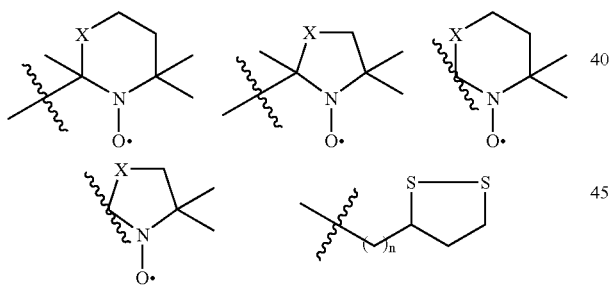

wherein X is selected from carbon, oxygen, and sulfur, and n is an integer from 1 to 15.

6. A β-agonist compound according to claim 1, wherein $R^2$ is selected from the following structures:

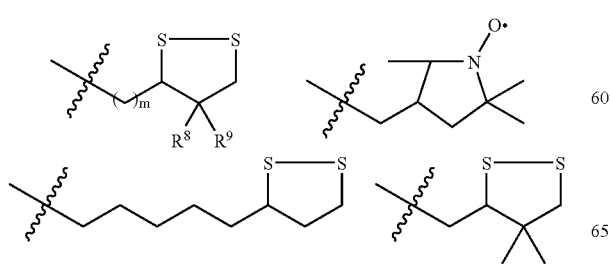

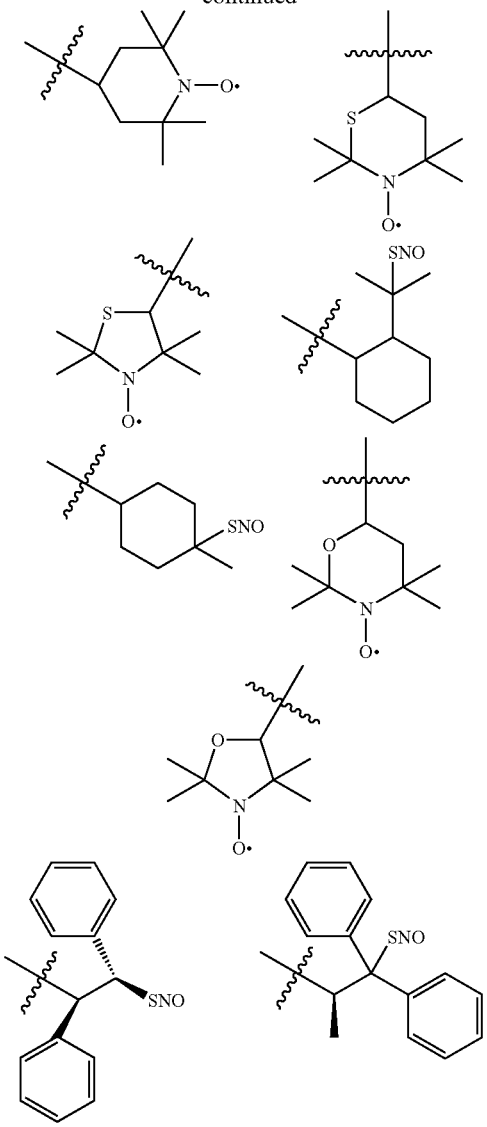

wherein m is 1-6 and $R^8$ and $R^9$ are independently $C_1$-$C_3$ alkyl or —H.

7. A β-agonist compound according to claim 1 having the formula:

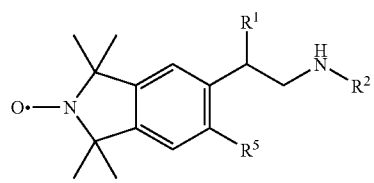

or its salt of a solvate thereof or an optical isomer thereof; wherein $R^1$ is SNO;

$R^5$ is hydrogen; and $R^2$ is a moiety selected from a nitroxide free radical having the nitrogen atom within a 5-, 6- or 7-membered saturated ring and which is substituted by up to four methyl groups at positions alpha to the nitrogen, sulfhydryl or dithiol moiety in oxidized or reduced form, —ONO, —ONO₂, and —SNO, wherein said moiety is connected to the —NH group directly or via a linker made of $C_1$-$C_6$ alkyl, and which linker is

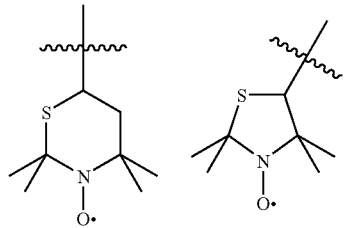

optionally substituted by one or more phenyl groups.

8. A multifunctional β-agonist compound according to claim 1 having one of the following structures:

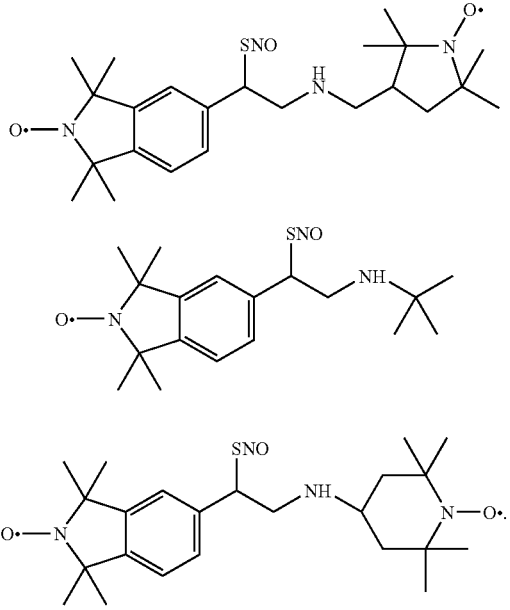

9. A process of preparing an agonist according to claim 1 being a compound of the formula:

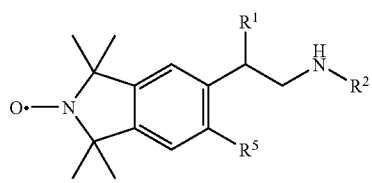

or its salt, wherein $R^1$ is —SNO;

$R^2$ is ROS scavenger group or a NO donor group connected to the —NH group via a linker made of $C_5$-$C_8$ cyclic alkyl, or straight or branched $C_1$-$C_{15}$ alkyl, wherein said ROS scavenger group is selected from a nitroxide free radical, alkenyl, sulfhydryl or dithiol moiety in oxidized or reduced form, and aryl, and wherein said NO donor group is selected from —ONO, —ONO₂, and —SNO or $R^2$ is $C_5$-$C_8$ cyclic alkyl, or straight or branched $C_1$-$C_{15}$ alkyl;

and $R^5$ is selected from the group consisting of —H and straight or branched chain $C_1$-$C_{15}$ alkyl;

and whereas any of said alkyl groups is optionally substituted with one or more functional groups selected from hydroxyl, mercapto, aryl, alkenyl, nitro, and alkoxyl;

which process comprises reacting a chiral or non-chiral epoxide or thioepoxide of the formula

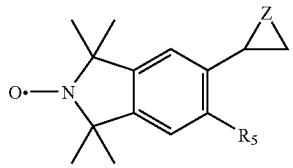

with an amine of the formula $H_2N$—$R^2$ wherein Z is oxygen or sulfur;

$R^2$ is a $C_5$-$C_8$ cyclic alkyl, or straight or branched $C_1$-$C_{15}$ alkyl linked to a group selected from a nitroxide free radical, alkenyl, sulfhydryl or dithiol moiety in oxidized or reduced form, aryl, —ONO, —ONO₂, and —SNO; wherein said alkyl is optionally substituted with one or more functional groups selected from hydroxyl, mercapto, aryl, alkenyl, nitro, alkoxyl, $C_1$-$C_5$ alkyl, $C_1$-$C_5$ alkoxy, phenyl, and —CH₂OH;

and $R^5$ is selected from the group consisting of —H and straight or branched chain $C_1$-$C_{15}$ alkyl.

10. A process according to claim 9, wherein said epoxide is prepared from N-benzylphthalimide.

11. A process according to claim 9, further comprising converting —SH groups to —SNO groups in the presence of HCl and NaNO₂.

12. A composition comprising a multifunctional β-agonist compound of claim 1, or a salt thereof or a solvate thereof or an optical isomer thereof, for use as a medicament.

13. A pharmaceutical composition comprising a β-agonist compound of any one of claims 1 to 8, or a salt thereof or a solvate thereof or an optical isomer thereof.

14. A pharmaceutical composition according to claim 13, further comprising carriers, adjuvants, and excipients.

* * * * *